US007244564B2

(12) United States Patent
Rothschild et al.

(10) Patent No.: US 7,244,564 B2
(45) Date of Patent: Jul. 17, 2007

(54) HMGA ALLELES AND USE OF THE SAME AS GENETIC MARKERS FOR GROWTH, FATNESS, MEAT QUALITY, AND FEED EFFICIENCY TRAITS

(75) Inventors: Max F. Rothschild, Ames, IA (US); Kwan-Suk Kim, Ames, IA (US); Nguyet Thu Nguyen, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 606 days.

(21) Appl. No.: 10/388,703

(22) Filed: Mar. 14, 2003

(65) Prior Publication Data

US 2004/0029145 A1 Feb. 12, 2004

Related U.S. Application Data

(60) Provisional application No. 60/364,959, filed on Mar. 15, 2002.

(51) Int. Cl.
*C12O 1/70* (2006.01)
*C12P 19/34* (2006.01)

(52) U.S. Cl. .......................... 435/6; 435/91.2; 436/501

(58) Field of Classification Search ...................... None
See application file for complete search history.

(56) References Cited

FOREIGN PATENT DOCUMENTS

| WO | WO 98/30689 | 7/1998 |
|----|-------------|--------|
| WO | PCT/US03/08027 | 3/2003 |

OTHER PUBLICATIONS

Vincek et al. (Mammalian Genome 5, 376-379 (1994)).*
Mummidi et al (2000) The Journal of Biological Chemistry, vol. 275, No. 25, pp. 18946-18961, 2000.*
Huang et al (2004) Genet. Sel. Evol. 36 (2004) 481-486.*
Juppner (Bone vol. 17, No. 2, Supplement, Aug. 1995: 39S-42S).*
PIC Technical Update, 2003, PIC USA, 2003 Insert, three pages.*
Thisted et al. www.stat.uchicago.edu/~thisted, pp. 1-6.*
Anand et al., "In vivo modulation of Hmgic reduces obesity", Nature Genetics, vol. 24:377-380 (2000).
Kim et al., "Mapping if the HMG-I Gene Family in the Pig", Presented in the Animal cytogenetics and gene mapping meeting, Jul. 15-19, 2001. University of California Davis.
Melillo et al., "Critical Role of the HMGI(Y) Proteins in Adipocytic Cell Growth and Differentiation", Molecular and Cellular Biology (2001) vol. 21(7) 2485-2495.
Ashar, H. R., et al. "Disruption of the Architectural Factor HMGI-C: DNA-Binding AT Hook Motifs Fused in Lipomas to Distinct Transcriptional Regulatory Domains" Cell, vol. 82, 57-65, Jul. 14, 1995.
Geurts, Jan M. W., et al. "Molecular Characterization of a Complex Chromosomal Rearrangement in a Pleomorphic Salivary Gland Adenoma Involving the 3'-UTR of HMGI" Cancer Genet Cytogenet 95:198-205 (1997).
Ishwad, C. S., et al. "The high mobility group I-C gene (HMGI-C): polymorphism and genetic localization" Hum Genet (1997) 99:103-105.

\* cited by examiner

*Primary Examiner*—Juliet C. Switzer
(74) *Attorney, Agent, or Firm*—McKee, Voorhees & Sease, P.L.C.

(57) ABSTRACT

Disclosed herein are genetic markers for animal growth, fatness, meat quality, and feed efficiency, methods for identifying such markers, and methods of screening animals to determine those more likely to produce desired growth, fatness, meat quality, and feed efficiency and preferably selecting those animals for future breeding purposes. The markers are based upon the presence or absence of certain polymorphisms in an HMGA nucleotide sequence.

14 Claims, 6 Drawing Sheets

```
  1  CCAACACCTA AAAGACCTCG GGGCCGACCA AAGGGGAGCA AAAACAAGGG
 51  CGCYGCCAAG ACCCGGGTGA GGCTTGAAGG GGTGGCTCCT GGTGGAGGGA
101  AGTGGGAAGT AACCCCCCGC CCCCTGCAAG CAGCTGAGGG AGGTCTGGGA
151  AGGGGTGGGC TTGTCCTGAT TCTCTGCATG CCCTTTCTCT GGTACGTGGG
201  CCCGATGGGT CTTGGCTAGT TGAGGAAAGT GGGGTGATGG CCGAGGCCTA
251  ACTTCTAGGG CCTTGTCTTG CCCAGGACAC TGGGGAAGTC AAGTCAGATG
301  TCCAGAGCT TTCCTGGTCT GGAGGGAGGC CAGTTGGGCA GAATGGAGGG
351  CTGTTCCCCC TGGGCTGAGA TGTCACCTCC CCCCAACCC CAGGCCGCCT
401  GGGTCCTGAG GGTGGGGGAG CAGGCAAGGC CAGATCTACA GTGGCATTGG
451  CCTTTGGAGA AGTTGTTTTG TTTTTTATTT TATTTTTTCT AAGACACGAC
501  TCATATCCTC TGAGTCACGG GTGAAGGAGG GAGTGGGGGC GTGTGTGTGT
551  ATGTTGGGGT GGGGGGCGGT GTGGCYGGCC AGTCATCCCC AGCTGGACTC
601  CGGTGGGCCT GCTGGGCTGA GAGTCCCGGC TGCCCCTCCC TGCTCGCCCT
651  CGCCCTCCAG GGCACTGGTC ACTGCGGGGC ACCCGCCATT GGGTGAGCAC
701  TGT
```

Fig. 1

```
   1  ACTGAAGAGA CATCCTCACA GAAGTCTGCA GAAGAGGATT AGGAGGCKCC
  51  AACATTCAAC GTCCACCTCA GCAGCAGTTG AATCTTTTGA AGGGAGAACT
 101  ACTTACTCCC TATTGCCATG GTTTTTCCAC TTTCATCTGG GGTTGCAGGG
 151  GAAGGGTGGG GGTGGGGTGG GAGGAGAAGG GACATAACCT TGAAAAGGAC
 201  TGTATTAATC ACCTTCTTTG TAATCCCTTC ACAGTCCCAG GTTTAGTGGA
 251  AAACTGCTGT AAACACAGGA GACACAGTTT AACAATGCAA CTTTTAATGA
 301  CTGTTTTCAT TTTCCTTAAC CTACTAATAG TTTGTGGATC TGATGAGCAG
 351  GAGTGGGTGG GTGAGAAAAA CTCTGAATGG GTTTAGCCAA TCACTGTACT
 401  GCATCCAAAC CAGAAACGTG TCACCTGCGT GACAGTGGGC ATTCCTCTAG
 451  GCAAGGTGCA GTAGGAAATG CTGCCCACCT CAGACGTCAC CCAGCCCCCT
 501  CTCAGTGGTG AAGCTTCTGT TTAGAACACC AAAGATAGGA CTAGATACTA
 551  CTTACTTTCT CATATAACCT GGTAGACACT TACTTGATGA TGTTTTTATT
 601  TTTACCTTTA TTTCTAAGTG AGAGGAAATG CTGATGTATC YTTTCATCCA
 651  ACTAACCAGA AAAGGTGATG TTCTCTTTTC AAAAAGGGAA GTAAGCAAAC
 701  TCAGATTGCC AACTCCTATA TTTATGGATG CTATACATTG CTTATTTAAT
 751  ACACAGTTAA CAGTAATGGT GAGTTTTAAT TCTCTCCGTA GCGCCTTTGG
 801  TAATTCACAA TAGTGATGGA TCTAATGGTT CTAGCATTTT AAGAAACCTA
 851  GACAAGTAAA ATTATTCTCT TTATGATTTC ATGAAAAGGT ACAACAGAAT
 901  AACCCATGAT GAACTTACCT GGATTATGAG ACGGGAGAAG CAAAATCTAA
 951  ATCTATTTTG CTATAGTTAT ACTACAATTT AAAGAACAAC AACAAAGCAG
1001  GCTCTCTTGT CTCTTTCTTT YTCTCTCTGT CTCTCTCTCC ATTGTGTATG
1051  AGTTTCTGTG AAAGATCTAA ATACCATGTT CCTCAAATGA AGCTTATGTG
1101  TTACTCCAGG TAATACGTTT TGACATAGGA TGGTTGGCTG AAGTGCTTTT
1151  CTTTGACATC AGCGYCGC..  ..........  ..........  ..........
```

Fig.2

CONSENSUS SEQUENCE OF THE PIG *HMGA1*

```
  1  CCAACACCTA AAAGACCTCG GGGCCGACCA AAGGGGAGCA AAAACAAGGG
 51  CGCYGCCAAG ACCCGGGTGA GGCTTGAAGG GGTGGCTCCT GGTGGAGGGA
101  AGTGGGAAGT AACCCCCCGC CCCCTGCAAG CAGCTGAGGG AGGTCTGGGA
151  AGGGGTGGGC TTGTCCTGAT TCTCTGCATG CCCTTTCTCT GGTACGTGGG
201  CCCGATGGGT CTTGGCTAGT TGAGGAAAGT GGGGTGATGG CCGAGGCCTA
251  ACTTCTAGGG CCTTGTCTTG CCCAGGACAC TGGGGAAGTC AAGTCAGATG
301  TCCCAGAGCT TTCCTGGTCT GGAGGGAGGC CAGTTGGGCA GAATGGAGGG
351  CTGTTCCCCC TGGGCTGAGA TGTCACCTCC CCCCAACCC CAGGCCGCCT
401  GGGTCCTGAG GGTGGGGGAG CAGGCAAGGC CAGATCTACA GTGGCATTGG
451  CCTTTGGAGA AGTTGTTTTG TTTTTTATTT TATTTTTTCT AAGACACGAC
501  TCATATCCTC TGAGTCACGG GTGAAGGAGG GAGTGGGGGC GTGTGTGTGT
551  ATGTTGGGGT GGGGGGCGGT GTGGCYGGCC AGTCATCCCC AGCTGGACTC
601  CGGTGGGCCT GCTGGGCTGA GAGTCCCGGC TGCCCCTCCC TGCTCGCCCT
651  CGCCCTCCAG GGCACTGGTC ACTGCGGGGC ACCCGCCATT GGGTGAGCAC
701  TGT
```

CONSENSUS SEQUENCE OF THE PIG *HMGA2*

```
   1  ACTGAAGAGA CATCCTCACA GAAGTCTGCA GAAGAGGATT AGGAGGCKGC
  51  AACATTCAAC GTCCACCTCA GCAGCAGTTG AATCTTTTGA AGGGAGAACT
 101  ACTTACTCCC TATTGCCATG GTTTTTCCAC TTTCATCTGG GGTTGCAGGG     Box 1
 151  GAAGGGTGGG GGTGGGGTGG GAGGAGAAGG GACATAACCT TGAAAAGGAC
 201  TGTATTAATC ACCTTCTTTG TAATCCCTTC ACAGTCCCAG GTTTAGTGGA
 251  AAACTGCTGT AAACACAGGA GACACAGTTT AACAATGCAA CTTTTAATGA
 301  CTGTTTTCAT TTTCCTTAAC CTACTAATAG TTTGTGGATC TGATGAGCAG
 351  GAGTGGGTGG GTGAGAAAAA CTCTGAATGG GTTAGCCAA TCACTGTACT
 401  GCATCCAAAC CAGAAACGTG TCACCTGCGT GACAGTGGGC ATTCCTCTAG
 451  GCAAGGTGCA GTAGGAAATG CTGCCCACCT CAGACGTCAC CCAGCCCCT
 501  CTCAGTGGTG AAGCTTCTGT TTAGAACACC AAAGATAGGA CTAGATACTA
 551  CTTACTTTCT CATATAACCT GGTAGACACT TACTTGATGA TGTTTTTATT
 601  TTTACCTTTA TTTCTAAGTG AGAGGAAATG CTGATGTATC YTTTCATCCA
 651  ACTAACCAGA AAAGGTGATG TTCTCTTTTC AAAAAGGGAA GTAAGCAAAC
 701  TCAGATTGCC AACTCCTATA TTTATGGATG CTATACATTG CTTATTTAAT
 751  ACACAGTTAA CAGTAATGGT GAGTTTAAT TCTCTCCGTA GCGCCTTTGG
 801  TAATTCACAA TAGTGATGGA TCTAATGGTT CTAGCATTTT AAGAAACCTA
 851  GACAAGTAAA ATTATTCTCT TTATGATTTC ATGAAAGGT ACAACAGAAT     Box 2
 901  AACCCATGAT GAACTTACCT GGATTATGAG ACGGGAGAAG CAAAATCTAA
 951  ATCTATTTTG CTATAGTTAT ACTACAATTT AAAGAACAAC AACAAAGCAG
1001  GCTCTCTTGT CTCTTTCTTT YTCTCTCTGT CTCTCTCTCC ATTGTGTATG
1051  AGTTTCTGTG AAAGATCTAA ATACCATGTT CCTCAAATGA AGCTTATGTG
1101  TTACTCCAGG TAATACGTTT TGACATAGGA TGGTTGGCTG AAGTGCTTTT
1151  CTTTGACATC AGGGYCGC.. .......... .......... ..........
```

Genetic Map of the pig chromosome 7 in the Berkshire and Yorkshire crossed family

Sex_averaged map (recomb. frac., Kosambi cM):

| | Marker | recomb. frac. | cM interval | Position |
|---|---|---|---|---|
| 10 | S0025 | | | 0.0 |
| | | 0.27 | 29.7 | |
| 9 | S0064 | | | 29.7 |
| | | 0.17 | 18.1 | |
| 8 | TNFB | | | 47.8 |
| | | 0.04 | 4.4 | |
| 0 | HMGA1 | | | 52.3 |
| | | 0.12 | 12.5 | |
| 7 | SWR1928 | | | 64.7 |
| | | 0.10 | 9.7 | |
| 2 | SW2040 | | | 74.4 |
| | | 0.09 | 9.0 | |
| 5 | SW252 | | | 83.5 |
| | | 0.06 | 6.1 | |
| 1 | SW632 | | | 89.6 |
| | | 0.05 | 5.5 | |
| 4 | SW1083 | | | 95.1 |
| | | 0.20 | 21.6 | |
| 3 | S0101 | | | 116.7 |
| | | 0.21 | 22.6 | |
| 6 | SW764 | | | 139.3 |

\* denotes recomb. frac. held fixed in this analysis log10_like = -1441.45

Sex-specific map (recomb. frac., Kosambi cM -- female, male):

| | Marker | female r.f. | female cM | female pos | male r.f. | male cM | male pos |
|---|---|---|---|---|---|---|---|
| 10 | S0025 | | | 0.0 | | | 0.0 |
| | | 0.30 | 35.4 | | 0.23 | 24.9 | |
| 9 | S0064 | | | 35.4 | | | 24.9 |
| | | 0.14 | 14.2 | | 0.21 | 22.1 | |
| 8 | TNFB | | | 49.6 | | | 47.0 |
| | | 0.06 | 5.6 | | 0.04 | 3.5 | |
| 0 | HMGA1 | | | 55.2 | | | 50.5 |
| | | 0.17 | 17.8 | | 0.08 | 7.9 | |
| 7 | SWR1928 | | | 72.9 | | | 58.4 |
| | | 0.08 | 7.8 | | 0.12 | 11.9 | |
| 2 | SW2040 | | | 80.7 | | | 70.3 |
| | | 0.12 | 12.1 | | 0.06 | 5.9 | |
| 5 | SW252 | | | 92.9 | | | 76.2 |
| | | 0.09 | 9.0 | | 0.04 | 3.8 | |
| 1 | SW632 | | | 101.8 | | | 80.0 |
| | | 0.05 | 5.0 | | 0.06 | 6.3 | |
| 4 | SW1083 | | | 106.9 | | | 86.3 |
| | | 0.21 | 21.8 | | 0.20 | 21.3 | |
| 3 | S0101 | | | 128.7 | | | 107.6 |
| | | 0.25 | 27.3 | | 0.17 | 17.8 | |
| 6 | SW764 | | | 156.0 | | | 125.5 | log10_like = -1428.65

Figure 6

SEQUENCE LISTING

<160> NUMBER OF SEQ ID NOS: 30

<210> SEQ ID NO 1
<211> LENGTH: 19
<212> TYPE: DNA
<213> ORGANISM: porcine

<400> SEQUENCE: 1
agaaggagcc cagcgaagt                                                    19

<210> SEQ ID NO 2
<211> LENGTH: 19
<212> TYPE: DNA
<213> ORGANISM: porcine

<400> SEQUENCE: 2
acagtgctca cccaatggc                                                    19

<210> SEQ ID NO 3
<211> LENGTH: 20
<212> TYPE: DNA
<213> ORGANISM: porcine

<400> SEQUENCE: 3
actgaagaga catcctcaca                                                   20

<210> SEQ ID NO 4
<211> LENGTH: 20
<212> TYPE: DNA
<213> ORGANISM: porcine

<400> SEQUENCE: 4
ctaaacctgg gactgtgaag                                                   20

<210> SEQ ID NO 5
<211> LENGTH: 22
<212> TYPE: DNA
<213> ORGANISM: porcine

<400> SEQUENCE: 5
gataggacta gatacaactt ac                                                22

<210> SEQ ID NO 6
<211> LENGTH: 20
<212> TYPE: DNA
<213> ORGANISM: porcine

<400> SEQUENCE: 6
ggatatattg catctctggc                                                   20

<210> SEQ ID NO 7
<211> LENGTH: 19
<212> TYPE: DNA
<213> ORGANISM: porcine

<400> SEQUENCE: 7
aagcagcctc cggtgagtc                                                    19

<210> SEQ ID NO 8
<211> LENGTH: 20
<212> TYPE: DNA
<213> ORGANISM: porcine

```
<400> SEQUENCE: 8
cacttcgctg ggctccttct                                              20

<210> SEQ ID NO 9
<211> LENGTH: 18
<212> TYPE: DNA
<213> ORGANISM: porcine

<400> SEQUENCE: 9
tctctagttc ctcattcc                                                18

<210> SEQ ID NO 10
<211> LENGTH: 19
<212> TYPE: DNA
<213> ORGANISM: porcine

<400> SEQUENCE: 10
cccaagacag aataaaaag                                               19

<210> SEQ ID NO 11
<211> LENGTH: 20
<212> TYPE: DNA
<213> ORGANISM: porcine

<400> SEQUENCE: 11
cctcttgtca ttttactgtc                                              20

<210> SEQ ID NO 12
<211> LENGTH: 18
<212> TYPE: DNA
<213> ORGANISM: porcine

<400> SEQUENCE: 12
accccacttt cctcaact                                                18

<210> SEQ ID NO 13
<211> LENGTH: 18
<212> TYPE: DNA
<213> ORGANISM: porcine

<400> SEQUENCE: 13
ctctgcctcc actctcta                                                18

<210> SEQ ID NO 14
<211> LENGTH: 18
<212> TYPE: DNA
<213> ORGANISM: porcine

<400> SEQUENCE: 14
tgccaaaggt gacaagac                                                18

<210> SEQ ID NO 15
<211> LENGTH: 19
<212> TYPE: DNA
<213> ORGANISM: porcine

<400> SEQUENCE: 15
ccaggaagga aaccaaggg                                               19

<210> SEQ ID NO 16
<211> LENGTH: 19
<212> TYPE: DNA
```

<213> ORGANISM: porcine

<400> SEQUENCE: 16
tgactcagca acctccacg                                                    19

<210> SEQ ID NO 17
<211> LENGTH: 19
<212> TYPE: DNA
<213> ORGANISM: porcine

<400> SEQUENCE: 17
ccaggaagga aaccaaggg                                                    19

<210> SEQ ID NO 18
<211> LENGTH: 19
<212> TYPE: DNA
<213> ORGANISM: porcine

<400> SEQUENCE: 18
tgactcagca acctccacg                                                    19

<210> SEQ ID NO 19
<211> LENGTH: 703
<212> TYPE: DNA
<213> ORGANISM: porcine

<400> SEQUENCE: 19
ccaacaccta aaagacctcg gggccgacca aagggagca aaaacaaggg cgcygccaag         60
acccgggtga ggcttgaagg ggtggctcct ggtggaggga agtgggaagt aaccccccgc       120
cccctgcaag cagctgaggg aggtctggga aggggtgggc ttgtcctgat tctctgcatg       180
ccctttctct ggtacgtggg cccgatgggt cttggctagt gaggaaagt ggggtgatgg        240
ccgaggccta acttctaggg ccttgtcttg cccaggacac tggggaagtc aagtcagatg       300
tcccagagct ttcctggtct ggagggaggc cagttgggca gaatggaggg ctgttccccc       360
tgggctgaga tgtcacctcc cccccaaccc caggccgcct gggtcctgag ggtgggggag       420
caggcaaggc cagatctaca gtggcattgg cctttggaga agttgttttg ttttttattt       480
tatttttct aagacacgac tcatatcctc tgagtcacgg gtgaaggagg gagtgggggc        540
gtgtgtgtgt atgttggggt gggggggcggt gtggcyggcc agtcatcccc agctggactc      600
cggtgggcct gctgggctga gagtcccggc tgcccctccc tgctcgccct cgccctccag       660
ggcactggtc actgcgggc acccgccatt gggtgagcac tgt                          703

<210> SEQ ID NO 20
<211> LENGTH: 1168
<212> TYPE: DNA
<213> ORGANISM: porcine

<400> SEQUENCE: 20
actgaagaga catcctcaca gaagtctgca gaagaggatt aggaggckcc aacattcaac        60
gtccacctca gcagcagttg aatcttttga agggagaact acttactccc tattgccatg       120
gtttttccac tttcatctgg ggttgcaggg aagggtggg ggtggggtgg gaggagaagg        180
gacataacct tgaaaggac tgtattaatc accttctttg taatcccttc acagtcccag        240
gtttagtgga aaactgctgt aaacacagga gacacagttt aacaatgcaa cttttaatga      300
ctgtttcat tttccttaac ctactaatag tttgtggatc tgatgagcag gagtgggtgg       360
gtgagaaaaa ctctgaatgg gtttagccaa tcactgtact gcatccaaac cagaaacgtg       420

| | |
|---|---|
| tcacctgcgt gacagtgggc attcctctag gcaaggtgca gtaggaaatg ctgcccacct | 480 |
| cagacgtcac ccagccccct ctcagtggtg aagcttctgt ttagaacacc aaagatagga | 540 |
| ctagatacta cttactttct catataacct ggtagacact tacttgatga tgtttttatt | 600 |
| tttaccttta tttctaagtg agaggaaatg ctgatgtatc ytttcatcca actaaccaga | 660 |
| aaaggtgatg ttctcttttc aaaaagggaa gtaagcaaac tcagattgcc aactcctata | 720 |
| tttatggatg ctatacattg cttatttaat acacagttaa cagtaatggt gagttttaat | 780 |
| tctctccgta gcgcctttgg taattcacaa tagtgatgga tctaatggtt ctagcatttt | 840 |
| aagaaaccta gacaagtaaa attattctct ttatgatttc atgaaaaggt acaacagaat | 900 |
| aacccatgat gaacttacct ggattatgag acgggagaag caaaatctaa atctattttg | 960 |
| ctatagttat actacaattt aaagaacaac aacaaagcag gctctcttgt ctctttcttt | 1020 |
| ytctctctgt ctctctctcc attgtgtatg agtttctgtg aaagatctaa ataccatgtt | 1080 |
| cctcaaatga agcttatgtg ttactccagg taatacgttt tgacatagga tggttggctg | 1140 |
| aagtgctttt ctttgacatc agcgycgc | 1168 |

<210> SEQ ID NO 21
<211> LENGTH: 1838
<212> TYPE: DNA
<213> ORGANISM: porcine
<220> FEATURE:
<221> NAME/KEY: misc_feature
<222> LOCATION: (725)..(725)
<223> OTHER INFORMATION: n can be any nucleotide

<400> SEQUENCE: 21

| | |
|---|---|
| aaaaagtttc tgggctagca cctgttcatg ggcctccttg agtggccctg ggttgggctc | 60 |
| tgcctccact ctctaaaagg aaattgaagc ccaagaagtt gacagtgttg aggagttggt | 120 |
| gcagagtgac tcagagccct gattctgtcc caccccctccc cccaaaggtc acgtgaggtt | 180 |
| aaaaggccac cctggcactt tgtgcgcccc agggagcttg gcccgtcagg ctgtggggac | 240 |
| cacctgttat atggtggaga tcttggtgtc tgttacaggg gggcagctgt ccccaagtga | 300 |
| ggggcagcgg ctggtggtga agcccagtta cttccttttc aggggggaga ggaaaggaat | 360 |
| tgaggtcgat ccctggcctt tagatggcag gcagtttgtg tacctgggcc tccggcttcc | 420 |
| ccgtctgtag gtggagagac ctggcggagc caggggtcat gagaagtcca atgggtgctg | 480 |
| gactcgagct gcctcatgga gggccctcag ctcgtgggga acttgtcctc ttcatctggt | 540 |
| cctttggcct ctcccagcck cctgttagcg gcggtcatgg ttgcgggggg atcagaaggg | 600 |
| gtgttgggtt actggaccac gcgcagcctg gggaaaccat agctgacgtg cctttgctgc | 660 |
| ccagagcctg tgctgcatgt agcagctttt tattctgtct tgggttagta caatttcagt | 720 |
| ggcantaatg ggcagggatc tggggctcca agatctggac agaatcctct ggggaggca | 780 |
| gcctggaggt cccttctgtt tgggggatg tcctctccca cctcctgcat cgccctggac | 840 |
| actggcacgt ccttcattgt acattgttca gttttttta ctgtcacagg aagcaaggg | 900 |
| gagaggcctt gcaaaggatg ttcagactgg gaacctgaat ccccagggct gtgcctgcca | 960 |
| tgattcctgt ggattctgga gtggggctgt cggggtgggg gtggggtggg gcagagactg | 1020 |
| tctggtgaaa gaggtgggac actggtgtct atgccctgac cgttccatct gtctttgcag | 1080 |
| aaggagccca gcgaagtgcc aacacctaaa agacctcggg gccgaccaaa ggggagcaaa | 1140 |
| aacaagggcg ccgccaagac ccgggtgagg cttgaagggg tggctcctgg tggagggaag | 1200 |

```
tgggaagtaa ccccagccc cctgcaagca gctgagggag gtctgggaag gggtgggctt   1260
gtcctgattc tctgcatgcc ctttctctgg tacgtgggcc cgatgggtct tggctagttg   1320
aggaaagtgg ggtgatggcc gaggcctaac ttctagggcc ttgtcttgcc caggacactg   1380
gggaagtcaa gtcagatgtc ccagagcttt cctggtctgg agggaggcca gttgggcaga   1440
atggagggct gttccccctg gctgagatg tcacctcccc cccaaccca ggccgcctgg   1500 gtcctgaggg tgggggagca ggcaaggcca gatctacagt ggcattggcc tttgagaag   1560 ttgttttgtt ttttatttta tttttctaa gacacgactc atatcctctg agtcacgggt   1620
gaaggaggga gtggggcgt gtgtgtgtat gttggggtgg ggggcggtgt ggcyggccag   1680
tcatccccag ctggactccg gtgggcctgc tgggctgaga gtcccggctg cccctccctg   1740
ctygccctcg ccctccaggg cactggtcac tgcggggcac ccgccattgg gtgagcactg   1800
tcagggacat ttttgacaat ggatcttttc tctgcaca                           1838
```

<210> SEQ ID NO 22
<211> LENGTH: 2484
<212> TYPE: DNA
<213> ORGANISM: porcine

<400> SEQUENCE: 22

```
ctggtaggag tcaggtgggt gtcaaacctt tgcctctgtt tacttctttg ggctagggag     60
gtgccaggcg tcttggcagc tgagagcaga actggcgggg cgcagagtcc ttcctgtaca    120
tgtgtgttct gtccacacgt gcacatacct ctcagaggag tgcgagcctc tgccagggtc    180
caagccgaag ggaccctgtg gtcaggcagg ccagtgctca caccggggta aagcacccag    240
cctttgtttc cacctcattg gggcacagtg catttgtgaa acgtggtaaa ggtgaattat    300
agaaacgcaa aatgacacat gtgtaagccc ggggttttca cttgttatat tcctcacaca    360
cagtattagc ctgttagttt actccaaagg tttctaatta cttaacttac tgtccatttc    420
tctagttcct cattccagta cagtaaaaag tttctgggct agcacctgtt catgggcctc    480
cttgagtggc cctgggttgg gctctgcctc cactctctaa aaggaaattg aagcccaaga    540
agttgacagt gttgaggagt tggtgcagag tgactcagag ccctgattct gtcccacccc    600 tcccccaaa ggtcacgtga ggttaaaagg ccaccctggc actttgtgcg ccccagggag    660
cttggcccgt caggctgtgg ggaccacctg ttatatggtg gagatcttgg tgtctgttac    720 agggggcag ctgtccccaa gtgaggggca gcggctggtg gtgaagccca gttacttcct    780
tttcaggggg gagaggaaag gaattgaggt cgatccctgg cctttagatg gcaggcagtt    840
tgtgtacctg ggcctccggc ttccccgtct gtaggtggag agacctggcg gagccagggg    900
tcatgagaag tctaatgggt gctggactcg agctgcctca tggagggccc tcagctcgtg    960
gggaacttgt cctcttcatc tggtcctttg gcctctccca gcctcctgtt agcggcggtc   1020
atggttgtgg gggatcaga agggtgttg ggttactgga ccacacgcag cctgggaaa    1080 ccatagctga cgtgccttg ctgcccagag cctgtgctgc atgtagcagc tttttattct   1140
gtcttgggct tagtacaatt tcagtgacac taatgggcag ggatctgggg ctccaagatc   1200
tggacagaat cctctggggg aggcagcctg gaggtccctt ctgtttgggg ggatgtcctc   1260
tcccacctcc tgcatcgccc tggacactgg cacgtccttc attgtacatt gttcagtttt   1320
cgtgactcta caaggtaggt cttgtcacct ttggcagatg agggaactg tagctcaagc    1380 ataaagcgtc ttgcccaaga tcttagacct aggcaatggc agagctggga tgcgaacaga   1440
gcagcctaag aagggggtttc tgtccccatg acacccttcc caatgggctt ctagcctctt   1500
```

-continued

```
gtcattttac tgtcacaggg aagcaagggg agaggccttg caaaggatgt tcagactggg      1560
aacctgaatc cccagggctg tgcctgccat gattcctgtg gattctggag tggggctgtc      1620
ggggtggggg tggggtgggg cagagactgt ctggtgaaag aggtgggaca ctggtgtcta      1680
tgccctgacc gttccatctg tctttgcaga aggagcccag cgaagtgcca cacctaaaa       1740 gacctcgggg ccgaccaaag gggagcaaaa acaagggcgc tgccaagacc cgggtgaggc      1800 ttgaagggt ggctcctggt ggagggaagt gggaagtaac ccccgcccc ctgcaagcag        1860 ctgagggagg tctgggaagg ggtgggcttg tcctgattct ctgcatgccc tttctctggt      1920
acgtgggccc gatgggtctt ggctagttga ggaaagtggg gtgatggccg aggcctaact      1980
tctagggcct tgtcttgccc aggacactgg ggaagtcaag tcagatgtcc cagagctttc      2040
ctggtctgga gggaggccag ttgggcagaa tggagggctg ttccccctgg gctgagatgt      2100
cacctccccc ccaaccccag gccgcctggg tcctgagggt gggggagcag gcaaggccag      2160
atctacagtg gcattggcct ttggagaagt tgttttgttt tttattttat tttttctaag      2220
acacgactca tatcctctga gtcacgggtg aaggagggag tggggcgtg tgtgtgtatg       2280 ttggggtggg gggcggtgtg gccggccagt catccccagc tggactccgg tgggcctgct     2340
gggctgagag tccggctgc ccctcccctgc tygccctcgc cctccagggc actggtcact      2400
gcggggcacc cgccattggg tgagcactgt cagggacatt tttgacaatg gatcttttct      2460
ctgaccatct agaaaaccac caca                                             2484
```

<210> SEQ ID NO 23
<211> LENGTH: 2484
<212> TYPE: DNA
<213> ORGANISM: porcine

<400> SEQUENCE: 23

```
ctggtaggag tcaggtgggt gtcaaacctt tgcctctgtt tacttctttg ggctagggag      60
gtgccaggcg tcttggcagc tgagagcaga actggcgggg cgcagagtcc ttcctgtaca      120
tgtgtgttct gtccacacgt gcacatacct ctcagaggag tgcgagcctc tgccagggtc      180
caagccgaag ggacccggtg gtcaggcagg ccagtgctca caccggggta aagcacccag      240
cctttgtttc cacctcatcg gggcacagtg catttgtgaa acgtggtaaa ggtgaattat      300
agaaacgcga aatgacacat gtgtaagccc ggggttttca cttgttatat tcctcacaca      360
cagtattagc ctgttagttt actccaaagg tttctaatta cttaacttac tgtccatttc      420
tctagttcct cattccagta cagtaaaaag tttctgggct agcacctgtt catgggcctc      480
cttgagtggc cctgggttgg gctctgcctc cactctctaa aaggaaattg aagcccaaga      540
agttgacagt gttgaggagt tggtgcagag tgactcagag ccctgattct gtcccacccc      600
tccccccaaa ggtcacgtga ggttaaaagg ccacccggc actttgtgcg ccccagggag       660
cttggcccgt caggctgtgg ggaccacctg ttatatggtg gagatcttgg tgtctgttac      720 agggggcag ctgtccccaa gtgaggggca gcggctggtg gtgaagccca gttacttcct       780
tttcaggggg gagaggaaag gaattgaggt cgatccctgg cctttagatg gcaggcagtt      840
tgtgtacctg ggcctccggc ttcccgtct gtaggtggag agacctggcg gagccagggg      900
tcatgagaag tctaatgggt gctggactcg agctgcctca tggagggccc tcagctcgtg      960
gggaacttgt cctcttcatc tggtcctttg gcctctccca gctcctgtt agcggcggtc       1020 atggttgtgg gggatcaga aggggtgttg ggttactgga ccacgcgcag cctggggaaa      1080
```

```
ccatagctga cgtgcctttg ctgcccagag cctgtgctgc atgtagcagc ttttattct    1140 gtcttgggct tagtacaatt tcagtggcac taatgggcag ggatctgggg ctccaagatc    1200
tggacagaat cctctggggg aggcagcctg gaggtccctt ctgtttgggg ggatgtcctc    1260
tcccacctcc tgcatcgccc tggacactgg cacgtccttc attgtacatt gttcagtttt    1320
cgtgactctg caaggtaggt cttgtcacct ttggcagatg aggggaactg tagctcaagc    1380
ataaagcatc ttgcccaaga tcttagacct aggcaatggc agagctggga tgcgaacaga    1440
gcagcctaag aagggtttc tgtccccatg acacccttcc caatgggctt ctagcctctt     1500
gtcattttac tgtcacaggg aagcaagggg agaggcttg caaggatgt tcagactggg      1560 aacctgaatc cccagggctg tgcctgccat gattcctgtg gattctggag tggggctgtc    1620
ggggtggggg tgggtggggg cagagactgt ctggtgaaag aggtgggaca ctggtgtcta    1680
tgccctgacc gttccatctg tctttgcaga aggagcccag cgaagtgcca acacctaaaa    1740
gacctcgggg ccgaccaaag gggagcaaaa acaaggcgc cgccaagacc cgggtgaggc     1800
ttgaaggggt ggctcctggt ggagggaagt gggaagtaac cccccgcccc ctgcaagcag    1860
ctgagggagg tctgggaagg ggtgggcttg tcctgattct ctgcatgccc tttctctggt    1920
acgtgggccc gatgggtctt ggctagttga ggaaagtggg gtgatggccg aggcctaact    1980
tctagggcct tgtcttgccc aggacactgg ggaagtcaag tcagatgtcc cagagctttc    2040
ctggtctgga gggaggccag ttgggcagaa tggagggctg ttccccctgg gctgagatgt    2100
cacctccccc ccaaccccag gccgcctggg tcctgagggt gggggagcag gcaaggccag    2160
atctacagtg gcattggcct ttggagaagt tgttttgttt tttattttat ttttctaag     2220 acacgactca tatcctctga gtcacgggtg aaggagggag tggggcgtg tgtgtgtatg     2280 ttggggtggg gggcggtgtg gctggccagt catccccagc tggactccgg tgggcctgct    2340
gggctgagag tcccggctgc ccctcccgc tcgcctcgc cctccagggc actggtcact      2400
gcggggcacc cgccattggg tgagcactgt cagggacatt tttgacaatg gatcttttct    2460
ctgaccatct agaaaaccac caca                                           2484
```

<210> SEQ ID NO 24
<211> LENGTH: 1950
<212> TYPE: DNA
<213> ORGANISM: porcine

<400> SEQUENCE: 24

```
ctggtaggag tcaggtgggt gtcaaacctt tgcctctgtt tacttctttg ggctagggag    60
gtgccaggcg tcttggcagc tgagagcaga actggcgggg cgcagagtcc ttcctgtaca    120
tgtgtgttct gtccacacgt gcacatacct ctcagaggag tgcgagcctc tgccagggtc    180
caagccgaag ggacccggtg gtcaggcagg ccagtgctca caccggggta agcacccag     240 cctttgtttc cacctcatcg gggcacagtg catttgtgaa acgtggtaaa ggtgaattat    300
agaaacgcga aatgacacat gtgtaagccc ggggttttca cttgttatat tcctcacaca    360
cagtattagc ctgttagttt actccaaagg tttctaatta cttaacttac tgtccatttc    420
tctagttcct cattccagta cagtaaaaag tttctgggct agcacctgtt catgggcctc    480
cttgagtggc cctggttgg gctctgcctc cactctctaa aaggaaattg aagcccaaga     540
agttgacagt gttgaggagt tggtgcagag tgactcagag ccctgattct gtcccacccc    600 tcccccaaa ggtcacgtga ggttaaaagg ccacctggc actttgtgcg ccccagggag      660
cttggcccgt caggctgtgg actttgtgcg ccccagggag cttggcccgt caggctgtgg    720
```

-continued

```
ggaccacctg ttatatggtg gagatcttgg tgtctgttac aggggggcag ctgtccccaa    780
gtgaggggca gcggctggtg gtgaagccca gttacttcct tttcaggggg gagaggaaag    840
gaattgaggt cgatccctgg cctttagatg gcaggcagtt tgtgtacctg gcctccggc    900
ttccccgtct gtaggtggag agacctggcg gagccagggg tcatgagaag tctaatgggt    960
gctggactcg agctgcctca tggagggccc tcagctcgtg gggaacttgt cctcttcatc   1020
tggtcctttg gcctctccca gcctcctgtt agcggcggtc atggttgtgg ggggatcaga   1080
aggggtgttg ggttactgga ccacgcgcag cctggggaaa ccatagctga cgtgcctttg   1140
ctgcccagag cctgtgctgc atgtagcagc ttttattct gtcttgggct tagtacaatt   1200
tcagtggcac taatgggcag ggatctgggg ctccaagatc tggacagaat cctctggggg   1260
aggcagcctg gaggtcccctt ctgtttgggg ggatgtcctc tcccacctcc tgcatcgccc   1320
tggacactgg cacgtccttc attgtacatt gttcagtttt cgtgactctg caaggtaggt   1380
cttgtcacct ttggcagatg agggaactg tagctcaagc ataaagcatc ttgcccaaga   1440
tcttagacct aggcaatggc agagctggga tgcgaacaga gcagcctaag aaggggtttc   1500
tgtccccatg acacccttcc caatgggctt ctagcctctt gtcatttac tgtcacaggg   1560
aagcaagggg agaggccttg caaaggatgt tcagactggg cacctgaatc cccagggctg   1620
tgcctgccat gattcctgtg gattctggag tggggctgtc ggggtggggg tggggtgggg   1680
cagagactgt ctggtgaaag aggtgggaca ctggtgtcta tgccctgacc gttccatctg   1740
tctttgcaga aggagcccag cgaagtgcca acacctaaaa gacctcgggg ccgaccaaag   1800
ttgaaggggt ggctcctggt ggagggaagt gggaagtaac ccccgccccc ctgcaagcag   1860
ctgagggagg tctgggaagg ggtgggcttg tcctgattct ctgcatgccc tttctctggt   1920
acgtgggccc gatgggtctt ggctagttga                                    1950
```

<210> SEQ ID NO 25
<211> LENGTH: 2404
<212> TYPE: DNA
<213> ORGANISM: porcine

<400> SEQUENCE: 25

```
ctggtaggag tcaggtgggt gtcaaaccctt tgcctctgtt tacttctttg ggctagggag     60
gtgccaggcg tcttggcagc tgagagcaga actggcgggg cgcagagtcc ttcctgtaca    120
tgtgtgttct gtccacacgt gcacatacct ctcagaggag tgcgagcctc tgccagggtc    180
caagccgaag ggaccggtg gtcaggcagg ccagtgctca caccggggta aagcacccag    240
cctttgtttc cacctcatcg gggcacagtg catttgtgaa acgtggtaaa ggtgaattat    300
agaaacgcga atgacacat gtgtaagccc gggttttca cttgttatat tcctcacaca    360
cagtattagc ctgttagttt actccaaagg tttctaatta cttaacttac tgtccatttc    420
tctagttcct cattccagta cagtaaaaag tttctgggct agcacctgtt catgggcctc    480
cttgagtggc cctgggttgg gctctgcctc cactctctaa aaggaaattg aagcccaaga    540
agttgacagt gttgaggagt tggtgcagag tgactcagag ccctgattct gtcccacccc    600
tccccccaaa ggtcacgtga ggttaaaagg ccacccctggc actttgtgcg ccccagggag    660
cttggcccgt caggctgtgg ggaccacctg ttatatggtg gagatcttgg tgtctgttac    720
agggggggcag ctgtccccaa gtgaggggca gcggctggtg gtgaagccca gttacttcct    780
tttcaggggg gagaggaaag gaattgaggt cgatccctgg cctttagatg gcaggcagtt    840
```

```
tgtgtacctg ggcctccggc ttccccgtct gtaggtggag gctggactcg agctgcctca     900
tggagggccc tcagctcgtg gggaacttgt cctcttcatc tggtcctttg gcctctccca     960
gcctcctgtt agcggcggtc atggttgtgg ggggatcaga aggggtgttg ggttactgga    1020
ccacgcgcag cctggggaaa ccatagctga cgtgcctttg ctgcccagag cctgtgctgc    1080
atgtagcagc ttttattct gtcttgggct tagtacaatt tcagtggcac taatgggcag     1140
ggatctgggg ctccaagatc tggacagaat cctctggggg aggcagcctg gaggtccctt    1200
ctgtttgggg ggatgtcctc tcccacctcc tgcatcgccc tggacactgg cacgtccttc    1260
attgtacatt gttcagtttt cgtgactctg caaggtaggc cttgtcacct ttggcagatg    1320
aggggaactg tagctcaagc ataaagcatc ttgcccaaga gcagcctaag aagggggtttc   1380 tgtccccatg acacccttcc caatgggctt ctagcctctt gtcatttac tgtcacaggg     1440 aagcaagggg agaggccttg caaggatgt tcagactggg aacctgaatc cccagggctg     1500
tgcctgccat gattcctgtg gattctggag tgggctgtc ggggtggggg tggggtgggg     1560
cagagactgt ctggtgaaag aggtgggaca ctggtgtcta tgccctgacc gttccatctg    1620
tctttgcaga aggagcccag cgaagtgcca acacctaaaa gacctcgggg ccgaccaaag    1680
gggagcaaaa acaagggcgc cgccaagacc cgggtgaggc ttgaagggggt ggctcctggt   1740 ggagggaagt gggaagtaac cccccgcccc ctgcaagcag ctgagggagg tctgggaagg    1800
ggtgggcttg tcctgattct ctgcatgccc tttctctggt acgtgggccc gatgggtctt    1860
ggctagttga ggaaagtggg gtgatggccg aggcctaact tctagggcct tgtcttgccc    1920
aggacactgg ggaagtcaag tcagatgtcc cagagctttc ctggtctgga gggaggccag    1980
ttgggcagaa tggagggctg ttccccctgg gctgagatgt cacctccccc ccaaccccag    2040
gccgcctggg tcctgagggt gggggagcag gcaaggccag atctacagtg gcattggcct    2100
ttggagaagt tgttttgttt tttattttat tttttctaag acacgactca tatcctctga    2160
gtcacgggtg aaggagggag tgggggcgtg tgtgtgtatg ttggggtggg gggcggtgtg    2220
gcyggccagt catccccagc tggactccgg tgggcctgct gggctgagag tcccggctgc    2280
ccctccctgc tcgccctcgc cctccagggc actggtcact gcggggcacc cgccattggg    2340
tgagcactgt cagggacatt tttgacaatg gatcttttct ctgaccatct agaaaaccac    2400
caca                                                                 2404
```

<210> SEQ ID NO 26
<211> LENGTH: 1103
<212> TYPE: DNA
<213> ORGANISM: porcine

<400> SEQUENCE: 26

```
tggtaggtga agaggctggg aaagcagcgg cggcagcttg gctcctctgg ggaggctctt      60
aagactgggt ggagccccct gtcttgtgtg tccgatacag agagacagac ttttctgacc     120 tgcgggggcca cgagcgctgg gacttcgcac ttagccaggc ccaggaggga ggatctgccc    180
aggcccgggc tgttgggggg ctgtgtccac gagcagtgaa gcggcccagg tgcaaagcag    240
cccgcactcc ttgccctgcc ccactgggcc tggtctcacg ctctcttccc tcgacttcta    300
gaccaggctc agaacttcta gggcgaacga atgagggag ggatcaggtc cattttgacc      360
ctggggcagg aggaagcagc agcagtggag ccccatcctg gggcgggtgg tgtccgtgtt    420
gggtggcagc tgaggtggga cacctcctca ccaggaggca ccatccactt ctgggcccca    480
aatagctgag gccagaggct gcctgcaggg ggcgcactgc agtgagggcc accagggcct    540
```

```
tcctctaggc ctcccctgct ccccacctgt gctccctggg gccttctttc ctccaccgcc      600
accaccatca ctgggtgcag ggggtgaggg ggtgagggga tgctggcagg gccccaagag      660
tgagtaacag gaaacaagtt gttttggagt ttgtgcctgg cacgggggcc cccatgtggt      720
gtcccaacat tccggcccag tgagtgagcc ccacacttcc ccttcctccc cgccctggcc      780
tggggtcagc ccgcggccag cctgttgtgg ccgctccaca gcccagcagc tgcccctgcg      840
ggccaaggcc acctgggtcc ccggcaccca ccagtgcagt gaggggctc attgcaccct       900 ccaggcaccc tgtcccattt cctcccctga ccacctccct gctcccccca cacccagcc      960 agtcacttcc tccagcctag tgctgccctg ggccctgcca ggtccctgcc ttgggcctgg     1020
gggccaaggg cctggctcgg tgagagcagc ccatgtgtgt ggtttttttc cctcccttta    1080
aattcttcct tttttatgaa tga                                            1103

<210> SEQ ID NO 27
<211> LENGTH: 1103
<212> TYPE: DNA
<213> ORGANISM: porcine

<400> SEQUENCE: 27
tggtaggtga agaggctggg aaagcagcgg cggcagcttg gctcctctgg ggaggctctt       60
aagactgggt ggagccccct gtcttgtgtg tccgatacag agagacagac ttttctgacc      120
tgcggggcca cgagcgctgg gacttcgcac ttagccaggc ccaggaggga ggatctgccc      180
aggcccgggc tgttggggg ctgtgtccac gagcagtgaa gcggcccagg tgcaaagcag       240
cccgcactcc ttgccctgcc ccactgggcc tggtctcacg ctctcttccc tcgacttcta     300
gaccaggctc agaacttcta gggcgaacga atgagggag ggatcaggtc cattttgacc      360
ctggggcagg aggaagcagc agcagtggag ccccatcctg gggcgggtgg tgtccgtgtt     420
gggtggcagc tgaggtggga cacctcctca ccaggaggca ccatccactt ctgggcccca     480
aatagctgag gccagaggct gcctgcaggg ggcgcactgc agtgagggcc accagggcct     540
tcctctaggc ctcccctgct ccccacctgt gctccctggg gccttctttc ctccaccgcc     600
accaccatca ctgggtgcag ggggtgaggg ggtgagggga tgctggcagg gccccaagag     660
tgagtaacag gaaacaagtt gttttggagt ttgtgcctgg cacgggggcc cccatgtggt    720
gtcccaacat tccggcccag tgagtgagcc ccacacttcc ccttcctccc cgccctggcc    780
tggggtcagc ccgcggccag cctgttgtgg ccgctccaca gcccagcagc tgcccctgcg    840
ggccaaggcc acctgggtcc ccggcaccca ccagtgcagt gaggggctc attgcaccct      900 ccaggcaccc tgtcccattt cctcccctga ccacctccct gctcccccca cacccagcc     960 agtcacttcc tccagcctag tgctgccctg ggccctgcca ggtccctgcc ttgggcctgg    1020
gggccaaggg cctggctcgg tgagagcagc ccatgtgtgt ggtttttttc cctcccttta   1080
aattcttcct tttttatgaa tga                                            1103

<210> SEQ ID NO 28
<211> LENGTH: 1102
<212> TYPE: DNA
<213> ORGANISM: porcine
<220> FEATURE:
<221> NAME/KEY: misc_feature
<222> LOCATION: (949)..(949)
<223> OTHER INFORMATION: n is any nucleotide
<220> FEATURE:
<221> NAME/KEY: misc_feature
<222> LOCATION: (957)..(957)
```

<223> OTHER INFORMATION: n is any nucleotide

<400> SEQUENCE: 28

| | | |
|---|---|---|
| tggtaggtga agaggctggg aaagcagcgg cggcagcttg gctcctctgg ggaggctctt | 60 |
| aagactgggt ggagccccct gtcttgtgtg tccgatacag agagacagac ttttctgacc | 120 |
| tgmggggcca cgagcgctgg gacttcgcac ttagccaggc ccaggaggga ggatctgccc | 180 |
| aggcccgggc tgttgggggg ctgtgtccac gagcagtgaa gcggcccagg tgcaaagcag | 240 |
| cccgcactcc ttgccctgcc ccactgggcc tggtctcacg ctctcttccc tcgacttcta | 300 |
| gaccaggctc agaacttcta gggcgaacga atgagggag ggatcaggtc cattttgacc | 360 |
| ctggggcagg aggaagcagc agcagtggag ccccatcctg gggcgggtgg tgtccgtgtt | 420 |
| gggtggcagc tgaggtggga cacctcctca ccaggaggca ccatccactt ctgggcccca | 480 |
| aatagctgag gccagaggct gcctgcaggg ggcgcactgc agtgagggcc accagggcct | 540 |
| tcctctaggc ctcccctgct ccccacctgt gctccctggg gccttctttc ctccaccgcc | 600 |
| accaccatca ctgggtgcag ggggtgaggg ggtgagggga tgctggcagg gccccaagag | 660 |
| tgagtaacag gaaacaagtt gttttggagt ttgtgcctgg cacgggggcc cccatgtggt | 720 |
| gtcccaacat tccggcccag tgagtgagcc ccacacttcc ccttcctccc cgccctggcc | 780 |
| tggggtagcc cgcggccagc ctgttgtggc cgctccacag cccagcagct gccctgcgg | 840 |
| gccaaggcca cctgggtccc cggcacccac cagtgcagtg aggggctca ttgcaccctc | 900 |
| caggcacct gtcccatttc ctcccctgac cactcccctg ctccccccnc cacccancca | 960 |
| gtcacttcct ccagcctagt gctgccctgg gccctgccag gtccctgcct tgggcctggg | 1020 |
| ggccaagggc ctggctcgt gagagcagcc catgtgtgtg gttttttttcc ctcccttttaa | 1080 |
| attcttcctt ttttatgaat ga | 1102 |

<210> SEQ ID NO 29
<211> LENGTH: 1059
<212> TYPE: DNA
<213> ORGANISM: porcine

<400> SEQUENCE: 29

| | | |
|---|---|---|
| tggtaggtga agaggctggg aaagcagcgg cggcagcttg gctcctctgg ggaggctctt | 60 |
| aagactgggt ggagccccct gtcttgtgtg tccgatacag agagacagac ttttctgacc | 120 |
| tgcggggcca cgagcgctgg gacttcgcac ttagccaggc ccaggaggga ggatctgccc | 180 |
| aggcccgggc tgttgggggg ctgtgtccac gagcagtgaa gcggcccagg tgcaaagcag | 240 |
| cccgcactcc ttgccctgcc ccactgggcc tggtctcacg ctctcttccc tcgacttcta | 300 |
| gaccaggctc agaacttcta gggcgaacga atgagggag ggatcaggtc cattttgacc | 360 |
| ctggggcagg aggaagcagc agcagtggag ccccatcctg gggcgggtgg tgtccgtgtt | 420 |
| gggtggcagc tgaggtggga cacctcctca ccaggaggca ccatccactt ctgggcccca | 480 |
| aatagctgag gccagaggct gcctgcaggg ggcgcactgc agtgagggcc accagggcct | 540 |
| tcctctaggc ctcccctgct ccccacctgt gctccctggg gccttctttc ctccaccgcc | 600 |
| accaccatca ctgggtgcag ggggtgaggg ggtgagggga tgctggcagg gccccaagag | 660 |
| tgagtaacag gaaacaagtt gttttggagt ttgtgctggc acgggggccc ccatgtggtg | 720 |
| tcccaacatt ccggcccagt gagtgagccc cacacttccc tttcctcccc gccctggcct | 780 |
| ggggtcagcc cgcggccagg gccaaggcca cctgggtccc cggcacccac cagtgcagtg | 840 |
| aggggctca ttgcaccctc caggcaccct gtcccatttc ctcccctgac cactcccctg | 900 |

-continued

```
ctccccccac cacccagcca gtcattcctc cagctagtgc tgccctgggc cctgccaggt    960
ccctgccttg ggcctggggg ccaagggctg gctcggtgag agcagcccat gtgtgtggtt   1020
tttttccctc cctttaaatt cttccttttt tatgaatga                          1059

<210> SEQ ID NO 30
<211> LENGTH: 1103
<212> TYPE: DNA
<213> ORGANISM: porcine

<400> SEQUENCE: 30
tggtaggtga agaggctggg aaagcagcgg cggcagcttg gctcctctgg ggaggctctt     60
aagactgggt ggagccccct gtcttgtgtg tccgatacag agagacagac ttttctgacc    120
tgcggggcca cgagcgctgg gacttcgcac ttagccaggc ccaggaggga ggatctgccc    180
aggcccgggc tgttgggggg ctgtgtccac gagcagtgaa gcggcccagg tgcaaagcag    240
cccgcactcc ttgccctgcc ccactgggcc tggtctcacg ctctcttccc tcgacttcta    300
gaccaggctc agaacttcta gggcgaacga aatgagggag ggatcaggtc cattttgacc    360
ctggggcagg aggaagcagc agcagtggag ccccatcctg gggcgggtgg tgtccgtgtt    420
gggtggcagc tgaggtggga cacctcctca ccaggaggca ccatccactt ctgggcccca    480
aatagctgag gccagaggct gcctgcaggg ggcgcactgc agtgagggcc accagggcct    540
tcctctaggc ctcccctgct ccccacctgt gctccctggg gccttctttc ctccaccgcc    600
accaccatca ctgggtgcag ggggtgaggg ggtgagggga tgctggcagg gccccaagag    660
tgagtaacag gaaacaagtt gttttggagt ttgtgcctgg cacgggggcc cccatgtggt    720
gtcccaacat tccggcccag tgagtgagcc ccacacttcc ccttcctccc cgccctggcc    780
tggggtcagc ccgcggccag cctgttgtgg ccgctccaca gcccagcagc tgcccctgcg    840
ggccaaggcc acctgggtcc ccggcaccca ccagtgcagt gaggggggctc attgcaccct    900 ccagcaccc tgtcccattt cctcccctga ccacctccct gctccccca ccacccagcc     960 agtcacttcc tccagcctag tgctgccctg ggccctgcca ggtccctgcc ttgggcctgg   1020
gggccaaggg cctggctcgg tgagagcagc ccatgtgtgt ggttttttttc cctcccttta   1080 aattcttcct ttttatgaa tga                                           1103
```

HMGA ALLELES AND USE OF THE SAME AS GENETIC MARKERS FOR GROWTH, FATNESS, MEAT QUALITY, AND FEED EFFICIENCY TRAITS

GRANT REFERENCE

Work for this invention was funded in part by USDA/CSREES contracts 2001-31200-06019, 2002-31200-06019, and 00-CRHR-0-6019.

FIELD OF THE INVENTION

This invention relates generally to the detection of genetic differences among animals. More particularly, the invention relates to genetic markers that are indicative of heritable phenotypes associated with improved growth, fatness, meat quality, and feed efficiency and other such economic traits in animals. Methods and compositions for use of these markers in genotyping of animals and selection are also disclosed.

BACKGROUND OF THE INVENTION

Genetic differences exist among individual animals as well as among breeds which can be exploited by breeding techniques to achieve animals with desirable characteristics. For example, Chinese breeds are known for reaching puberty at an early age and for their large litter size, while American breeds are known for their greater growth rates and leanness. However, heritability for desired traits is often low, and standard breeding methods which select individuals based upon phenotypic variations do not take fully into account genetic variability or complex gene interactions which exist.

Restriction fragment length polymorphism (RFLP) analysis has been used by several groups to study pig DNA. Jung et al., *Theor. Appl. Genet.*, 77:271–274 (1989), incorporated herein by reference, discloses the use of RFLP techniques to show genetic variability between two pig breeds. Polymorphism was demonstrated for swine leukocyte antigen (SLA) Class I genes in these breeds. Hoganson et al., *Abstract for Annual Meeting of Midwestern Section of the American Society of Animal Science*, Mar. 26–28, 1990, incorporated herein by reference, reports on the polymorphism of swine major histocompatibility complex (MHC) genes for Chinese pigs, also demonstrated by RFLP analysis. Jung et al., *Theor. Appl. Genet.*, 77:271–274 (1989), incorporated herein by reference, reports on RFLP analysis of SLA Class I genes in certain boars. The authors state that the results suggest that there may be an association between swine SLA/MHC Class I genes and production and performance traits. They further state that the use of SLA Class I restriction fragments, as genetic markers, may have potential in the future for improving pig growth performance.

The ability to follow a specific favorable genetic allele involves a novel and lengthy process of the identification of a DNA molecular marker for a major effect gene. The marker may be linked to a single gene with a major effect or linked to a number of genes with additive effects. DNA markers have several advantages; segregation is easy to measure and is unambiguous, and DNA markers are co-dominant, i.e., heterozygous and homozygous animals can be distinctively identified. Once a marker system is established selection decisions could be made very easily, since DNA markers can be assayed any time after a tissue or blood sample can be collected from the individual infant animal, or even an embryo.

The use of genetic differences in receptor genes has become a valuable marker system for selection. For example, U.S. Pat. Nos. 5,550,024 and 5,374,526 issued to Rothschild et al. disclose a polymorphism in the pig estrogen receptor gene which is associated with larger litter size, the disclosure of which is incorporated herein by reference. U.S. Pat. No. 5,935,784 discloses polymorphic markers in the pig prolactin receptor gene which are associated with larger litter size and overall reproductive efficiency.

The quality of raw pig meat is influenced by a large number of genetic and non-genetic factors. The latter include farm, transport, slaughter and processing conditions. Meat scientists have performed a substantial amount of research on these factors, which has led to considerable quality improvement. Part of the research has also been dedicated to the genetic background of the animals, and several studies have revealed the importance of genetic factors. This has made the industry aware that selective breeding of animals and the use of gene technology can play an important role in enhancing pork quality.

Information at DNA level can help to fix a specific major gene, but it can also assist the selection of quantitative trait for which we already select. Molecular information in addition to phenotypic data can increase the accuracy of selection and therefore the selection response. The size of the extra response in such a Marker Assisted Selection (MAS) program has been considered by many workers from a theoretical point of view. In general terms, MAS is more beneficial for traits with a low heritability and which are expensive to measure phenotypically. Although traits such as growth, fatness, meat quality, and feed efficiency are not typically considered in this, way there are still significant advantages for the use of markers for these traits. For example, Meuwissen and goddard considered the impact of MAS for different types of traits. The biggest impacts were for traits such as meat quality, where the trait is measured after slaughter and an additional response of up to 64% could be achieved with the incorporation of marker information. This figure was relatively small, 8%, for growth traits, that can be measured on the live animal. However, once the association has been demonstrated this marker information can be used before the animals are tested or selected phenotypically (see below) and in this situation a response of up to 38% was predicted.

Indeed, the best approach to genetically improve economic traits is to find relevant DNA-markers directly in the population under selection. Phenotypic measurements can be performed continuously on some animals from the nucleus populations of breeding organizations. Since a full assessment of most of these traits can only be done after slaughter, the data must be collected on culled animals and cannot be obtained on potential breeding animals.

This phenotypic data is collected in order to enable the detection of relevant DNA markers, and to validate markers identified using experimental populations or to test candidate genes. Significant markers or genes can then be included directly in the selection process. An advantage of the molecular information is that we can obtain it already at very young age of the breeding animal, which means that animals can be preselected based on DNA markers before the growing performance test is completed. This is a great advantage for the overall testing and selection system.

It can be seen from the foregoing that a need exists for identification of markers which may be used to improve economically beneficial characteristics in animals by identifying and selecting animals with the improved characteristics at the genetic level.

An object of the present invention is to provide a genetic marker based on or within an HMGA encoding nucleotide sequence which is indicative of favorable economic characteristics such as growth, fatness, meat quality, and feed efficiency.

Another object of the invention is to provide an assay for determining the presence of this genetic marker.

A further object of the invention is to provide a method of evaluating animals that increases accuracy of selection and breeding methods for the desired traits.

Yet another object of the invention is to provide a PCR amplification test which will greatly expedite the determination of presence of the marker(s).

Additional objects and advantages of the invention will be set forth in part in the description that follows, and in part will be obvious from the description, or may be learned by the practice of the invention. The objects and advantages of the invention will be attained by means of the instrumentality's and combinations particularly pointed out in the appended claims.

SUMMARY OF THE INVENTION

This invention relates to the discovery of alternate gene forms of the HMGA encoding nucleotide sequences which are useful for genetic identification of animals for tracing lineage or as genetic markers associated with growth, fatness, meat quality, and feed efficiency traits in animals. To the extent that these genes are conserved among species and animals, and it is expected that the different alleles disclosed herein will also correlate with variability in these gene(s) in other economic or meat-producing animals such as cattle, sheep, chicken, etc.

To achieve the objects and in accordance with the purpose of the invention, as embodied and broadly described herein, the present invention provides the discovery of alternate genotypes which provide a method for genetically typing animals and screening animals to determine those more likely to possess favorable growth, fatness, meat quality, and feed efficiency traits or to select against animals which have alleles indicating less favorable growth, fatness, meat quality, and feed efficiency traits. As used herein a "favorable growth, fatness, meat quality, and feed efficiency trait" means a significant improvement (increase or decrease) in one of many measurable growth, fatness, meat quality, and feed efficiency traits above the mean of a given population, so that this information can be used in breeding to achieve a uniform population which is optimized for growth, fatness, meat quality, and feed efficiency, this may include an increase in some traits or a decrease in others depending on the desired characteristics. For a review of some example economic traits the following may be consulted: Sosnicki, A. A., E. R. Wilson, E. B. Sheiss, A. deVries, 1998 "Is there a cost effective way to produce high quality pork?", *Reciprocal Meat Conference Proceedings*, Vol. 51.

Thus, the present invention provides a method for screening animals to identify those more likely to produce favorable growth, fatness, meat quality, and feed efficiency, and/or those less likely to produce favorable growth, fatness, meat quality, and feed efficiency to optimize breeding and selection techniques for the best growth, fatness, meat quality, and feed efficiency.

Methods for assaying for these traits generally comprises the steps 1) obtaining a biological sample from a animal; and 2) analyzing the genomic DNA or protein obtained in 1) to determine which HMGA allele(s) is/are present. Haplotype data which allows for a series of polymorphisms in the HMGA genes to be combined in a selection or identification protocol to maximize the benefits of each of these markers may also be used.

Since several of the polymorphisms may involve changes in amino acid composition of the HMGA protein or will be indicative of the presence of this change, assay methods may even involve ascertaining the amino acid composition of the HMGA protein. Methods for this type or purification and analysis typically involve isolation of the protein through means including fluorescence tagging with antibodies, separation and purification of the protein (i.e. through reverse phase HPLC system), and use of an automated protein sequencer to identify the amino acid sequence present. Protocols for this assay are standard and known in the art and are disclosed in Ausubel et. al.(eds.), Short Protocols in Molecular Biology Fourth ed. John Wiley and Sons 1999.

In a preferred embodiment a genetic sample is analyzed. Briefly, a sample of genetic material is obtained from an animal, and the sample is analyzed to determine the presence or absence of a polymorphism(s) in the HMGA nucleotide sequences that (are) correlated with improved growth, fatness, meat quality, and feed efficiency.

As is well known to those of skill in the art, a variety of techniques may be utilized when comparing nucleic acid molecules for sequence differences. These include by way of example, restriction fragment length polymorphism analysis, heteroduplex analysis, single strand conformation polymorphism analysis, denaturing gradient electrophoresis and temperature gradient electrophoresis.

In a preferred embodiment the polymorphism is a restriction fragment length polymorphism and the assay comprises identifying the animal HMGA genes from isolated genetic material; exposing the genes to a restriction enzyme that yields restriction fragments of the genes of varying length; separating the restriction fragments to form a restriction pattern, such as by electrophoresis or HPLC separation; and comparing the resulting restriction fragment pattern from an HMGA nucleotide sequences that are either known to have or not to have the desired markers. If an animal tests positive for the markers, such animal can be considered for inclusion in the breeding program. If the animal does not test positive for the marker genotype the animal can be culled from the group and otherwise used. Use of haplotype data can also be incorporated with the screening for multiple alleles for different aspects of growth, fatness, meat quality, and feed efficiency.

In a most preferred embodiment these genes are isolated by the use of primers and DNA polymerase to amplify a specific region of these genes which contain the polymorphism. Next the amplified region is digested with a restriction enzyme and fragments are again separated. Visualization of the RFLP pattern is by simple staining of the fragments, or by labeling the primers or the nucleoside triphosphates used in amplification.

In another embodiment, the invention comprises a method for identifying genetic markers for growth, fatness, meat quality, and feed efficiency in a particular population. Male and female animals of the same breed or breed cross or similar genetic lineage are bred, and growth, fatness, meat quality, and feed efficiency produced by each animal is determined. A polymorphism in one or both of the HMGA genes of each animal is identified and associated with the growth, fatness, meat quality, and feed efficiency. Preferably, RFLP analysis is used to determine the polymorphism.

In another embodiment, the invention comprises a method for identifying a genetic marker for growth, fatness, meat quality, and feed efficiency in any particular economic animal other than a animal. Based upon the highly conserved nature of this gene among different animals is it expected that with no more than routine testing as described herein this marker can be applied to different animal species to select for growth, fatness, meat quality, and feed efficiency based on the teachings herein. Male and female animals of the same breed or breed cross or similar genetic lineage are bred, and the growth, fatness, meat quality, and feed efficiency produced by each animal is determined and correlated. For other animals in which sequences are available a BLAST comparison of sequences may be used to ascertain whether the particular allele is analogous to the one disclosed herein. The analogous polymorphism will be present in other animals and in other closely related genes. The term "analogous polymorphism" shall be a polymorphism which is the same as any of those disclosed herein as determined by BLAST comparisons.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. In this case the Reference HMGA sequences. A reference sequence may be a subset or the entirety of a specified sequence; for example, as a segment of a full-length cDNA or gene sequence, or the complete CDNA or gene sequence.

(b) As used herein, "comparison window" includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., U.S.A.; the CLUSTAL program is well described by Higgins and Sharp, *Gene* 73:237–244 (1988); Higgins and Sharp, CABIOS 5:151–153 (1989); Corpet, et al., *Nucleic Acids Research* 16:10881–90 (1988); Huang, et al., *Computer Applications in the Biosciences* 8:155–65 (1992), and Pearson, et al., *Methods in Molecular Biology* 24:307–331 (1994). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et a., *Nucleic Acids Res.* 25:3389–3402 (1997). Software for performing BLAST analyses is publicly available, e.g., through the National Center for Biotechnology-Information (http://www.hcbi.nlm.nih.gov/).

This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity×from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Natl. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.,* 17:149–163 (1993)) and XNU (Claverie and States, *Comput. Chem.,* 17:191–201 (1993)) low-complexity filters can be employed alone or in combination.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.,* 4:11–17 (1988) e.g., as implemented in the program PC/GENE (Intelligenetics, Mountain View, Calif., U.S.A.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) (I) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or preferably at least 70%, 80%, 90%, and most preferably at least 95%.

These programs and algorithms can ascertain the analogy of a particular polymorphism in a target gene to those disclosed herein. It is expected that this polymorphism will exist in other animals and use of the same in other animals than disclosed herein involved no more than routine optimization of parameters using the teachings herein.

It is also possible to establish linkage between specific alleles of alternative DNA markers and alleles of DNA markers known to be associated with a particular gene (e.g. the HMGA genes discussed herein), which have previously been shown to be associated with a particular trait. Thus, in the present situation, taking one or both of the HMGA genes, it would be possible, at least in the short term, to select for animals likely to produce desired growth, fatness, meat quality, and feed efficiency, or alternatively against animals likely to produce less desirable growth, fatness, meat quality, and feed efficiency, indirectly, by selecting for certain alleles of a HMGA associated marker through the selection of specific alleles of alternative chromosome markers. As used herein the term "genetic marker" shall include not only the nucleotide polymorphisms disclosed by any means of assaying for the protein changes associated with the polymorphism, be they linked markers, use of microsatellites, or even other means of assaying for the causative protein changes indicated by the marker and the use of the same to influence the growth, fatness, meat quality, and feed efficiency of an animal.

As used herein, often the designation of a particular polymorphism is made by the name of a particular restriction enzyme. This is not intended to imply that the only way that the site can be identified is by the use of that restriction enzyme. There are numerous databases and resources available to those of skill in the art to identify other restriction enzymes which can be used to identify a particular polymorphism, for example http://darwin.bio.geneseo.edu which can give restriction enzymes upon analysis of a sequence and the polymorphism to be identified. In fact as disclosed in the teachings herein there are numerous ways of identifying a particular polymorphism or allele with alternate methods which may not even include a restriction enzyme, but which assay for the same genetic or proteomic alternative form.

The accompanying figures, which are incorporated herein and which constitute a part of this specification, illustrates one embodiment of the invention and, together with the description, serve to explain the principles of the invention.

DESCRIPTION OF THE FIGURES

FIG. 1 is the consensus sequence of the pig hmga1. (SEQ ID NO: 19).

Figure 5:
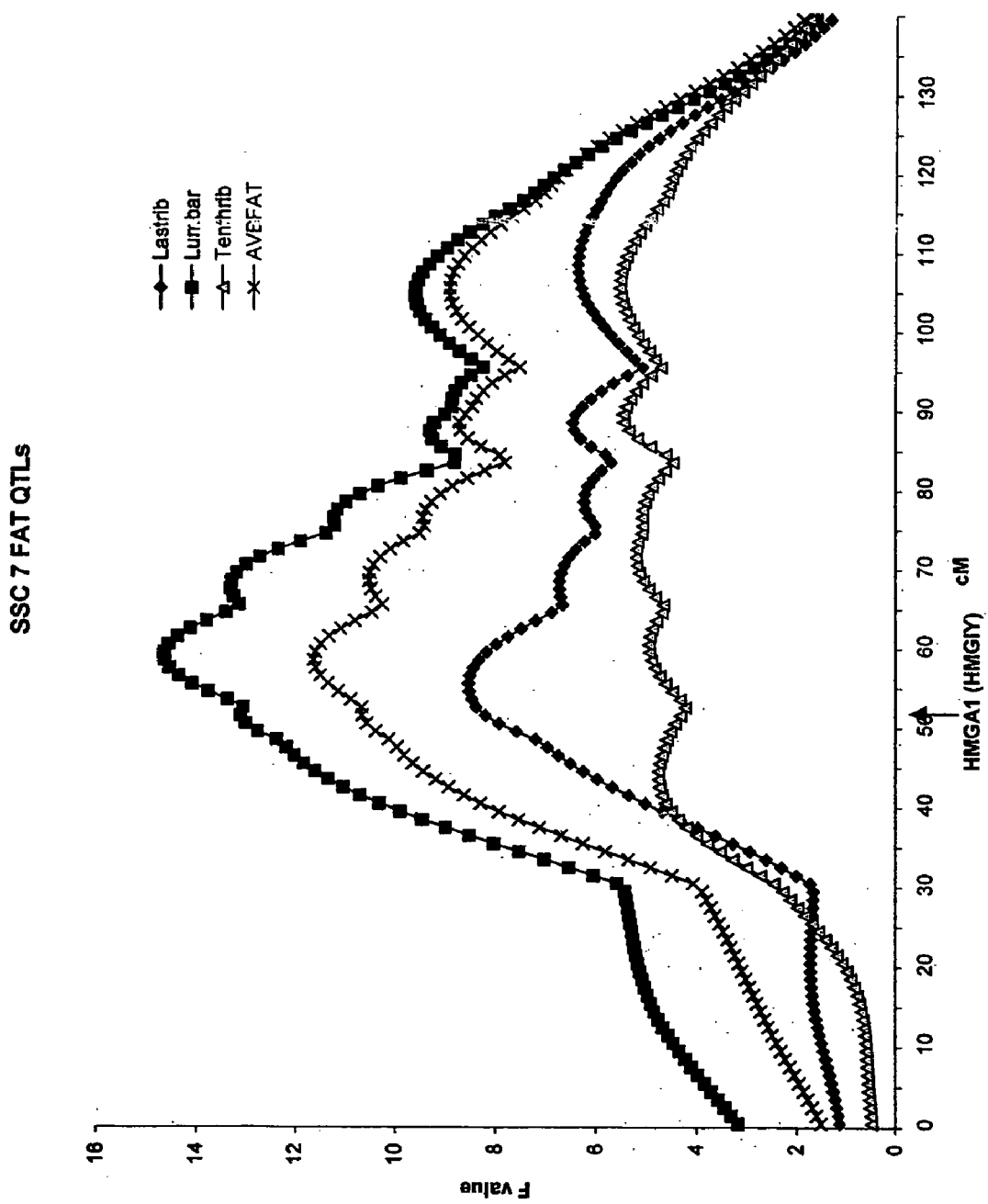

Two BanI recognition sites are indicated as underlined and bold. One of which contains the single nucleotide polymorphism at position 54. The NaeI polymorphic site (GCYGGC) is indicated as underlined.

Y=C or T

FIG. 2 is a consensus sequence of the pig hmga2. Length: 1168 Three HhaI recognition (GCGC) sites are underlined and two of them highlighted with gray contain DNA polymorphisms. SEQ ID NO:20

Box 1 is approximate PCR fragment of the Mix 1.

Box 2 is approximate PCR fragment of the Mix 2.

K=G or T

Y=C or T

DETAILED DESCRIPTION OF THE INVENTION

Reference will now be made in detail to the presently referred embodiments of the invention, which together with the following examples, serve to explain the principles of the invention.

The invention relates to genetic markers for economically valuable traits in animals. The markers represent alleles that are associated significantly with a growth, fatness, meat quality, and feed efficiency trait and thus provides a method of screening animals to determine those more likely to produce desired growth, fatness, meat quality, and feed efficiency (levels of one or all of these) when bred by identifying the presence or absence of a polymorphism in one or both of the HMGA nucleotide sequences, which is correlated with desired growth, fatness, meat quality, and feed efficiency.

Thus, the invention relates to genetic markers and methods of identifying those markers in an animal of a particular breed, strain, population, or group, whereby the animal is more likely to yield meat of desired growth, fatness, meat quality, and feed efficiency.

According to the invention, novel alleles of the HMGA nucleotide sequences have been identified which are associated with improved traits in animals. In one embodiment of the invention, novel porcine HMGA1 alleles identifiable by a Ban I or Nae I restriction site have been are shown to be associated with lower fat content and other such fat, growth, meat quality, and/or feed efficiency traits. In yet another embodiment a novel Hha I allele in the HMGA2 gene has been identified which is associated with fat and growth traits. In yet a further embodiment, the markers have been shown to have an additive effect together.

Any method of identifying the presence or absence of this marker may be used, including for example single-strand conformation polymorphism (SSCP) analysis, base excision sequence scanning (BESS), RFLP analysis, heteroduplex analysis, denaturing gradient gel electrophoresis, and temperature gradient electrophoresis, allelic PCR, ligase chain reaction direct sequencing, mini sequencing, nucleic acid hybridization, micro-array-type detection of an HMGA gene, or other linked sequences of the HMGA genes. Also within the scope of the invention includes assaying for protein conformational or sequences changes which occur in the presence of this polymorphism. The polymorphism may or may not be the causative mutation but will be indicative of the presence of this change and one may assay for the genetic or protein bases for the phenotypic difference.

The following is a general overview of techniques which can be used to assay for the polymorphisms of the invention.

In the present invention, a sample of genetic material is obtained from an animal. Samples can be obtained from blood, tissue, semen, etc. Generally, peripheral blood cells are used as the source, and the genetic material is DNA. A sufficient amount of cells are obtained to provide a sufficient amount of DNA for analysis. This amount will be known or readily determinable by those skilled in the art. The DNA is isolated from the blood cells by techniques known to those skilled in the art.

Isolation and Amplification of Nucleic Acid

Samples of genomic DNA are isolated from any convenient source including saliva, buccal cells, hair roots, blood, cord blood, amniotic fluid, interstitial fluid, peritoneal fluid, chorionic villus, and any other suitable cell or tissue sample with intact interphase nuclei or metaphase cells. The cells can be obtained from solid tissue as from a fresh or preserved organ or from a tissue sample or biopsy. The sample can contain compounds which are not naturally intermixed with the biological material such as preservatives, anticoagulants, buffers, fixatives, nutrients, antibiotics, or the like.

Methods for isolation of genomic DNA from these various sources are described in, for example, Kirby, DNA Fingerprinting, An Introduction, W. H. Freeman & Co. New York (1992). Genomic DNA can also be isolated from cultured primary or secondary cell cultures or from transformed cell lines derived from any of the aforementioned tissue samples.

Samples of animal RNA can also be used. RNA can be isolated from tissues expressing an HMGA gene as described in Sambrook et al., supra. RNA can be total cellular RNA, mRNA, poly A+ RNA, or any combination thereof. For best results, the RNA is purified, but can also be unpurified cytoplasmic RNA. RNA can be reverse transcribed to form DNA which is then used as the amplification template, such that the PCR indirectly amplifies a specific population of RNA transcripts. See, e.g., Sambrook, supra, Kawasaki et al., Chapter 8 in PCR Technology, (1992) supra, and Berg et al., Hum. Genet. 85:655–658 (1990).

PCR Amplification

The most common means for amplification is polymerase chain reaction (PCR), as described in U.S. Pat. Nos. 4,683, 195, 4,683,202, 4,965,188 each of which is hereby incorporated by reference. If PCR is used to amplify the target regions in blood cells, heparinized whole blood should be drawn in a sealed vacuum tube kept separated from other samples and handled with clean gloves. For best results, blood should be processed immediately after collection; if this is impossible, it should be kept in a sealed container at 4° C. until use. Cells in other physiological fluids may also be assayed. When using any of these fluids, the cells in the fluid should be separated from the fluid component by centrifugation.

Tissues should be roughly minced using a sterile, disposable scalpel and a sterile needle (or two scalpels) in a 5 mm Petri dish. Procedures for removing paraffin from tissue sections are described in a variety of specialized handbooks well known to those skilled in the art.

To amplify a target nucleic acid sequence in a sample by PCR, the sequence must be accessible to the components of the amplification system. One method of isolating target DNA is crude extraction which is useful for relatively large samples. Briefly, mononuclear cells from samples of blood, amniocytes from amniotic fluid, cultured chorionic villus cells, or the like are isolated by layering on sterile Ficoll-Hypaque gradient by standard procedures. Interphase cells are collected and washed three times in sterile phosphate buffered saline before DNA extraction. If testing DNA from peripheral blood lymphocytes, an osmotic shock (treatment of the pellet for 10 sec with distilled water) is suggested, followed by two additional washings if residual red blood cells are visible following the initial washes. This will prevent the inhibitory effect of the heme group carried by hemoglobin on the PCR reaction. If PCR testing is not performed immediately after sample collection, aliquots of $10^6$ cells can be pelleted in sterile Eppendorf tubes and the dry pellet frozen at $-20°$ C. until use.

The cells are resuspended ($10^6$ nucleated cells per 100 µl) in a buffer of 50 mM Tris-HCl (pH 8.3), 50 m KCl 1.5 mM $MgCl_2$, 0.5% Tween 20, 0.5% NP40 supplemented with 100 µg/ml of proteinase K. After incubating at 56° C. for 2 hr. the cells are heated to 95° C. for 10 min to inactivate the proteinase K and immediately moved to wet ice (snap-cool). If gross aggregates are present, another cycle of digestion in the same buffer should be undertaken. Ten µl of this extract is used for amplification.

When extracting DNA from tissues, e.g., chorionic villus cells or confluent cultured cells, the amount of the above mentioned buffer with proteinase K may vary according to the size of the tissue sample. The extract is incubated for 4–10 hrs at 50°–60° C. and then at 95° C. for 10 minutes to inactivate the proteinase. During longer incubations, fresh proteinase K should be added after about 4 hr at the original concentration.

When the sample contains a small number of cells, extraction may be accomplished by methods as described in Higuchi, "Simple and Rapid Preparation of Samples for PCR", in PCR Technology, Ehrlich, H. A. (ed.), Stockton Press, New York, which is incorporated herein by reference. PCR can be employed to amplify target regions in very small numbers of cells (1000–5000) derived from individual colonies from bone marrow and peripheral blood cultures. The cells in the sample are suspended in 20 µl of PCR lysis buffer (10 mM Tris-HCl (pH 8.3), 50 mM KCl, 2.5 mM $MgCl_2$, 0.1 mg/ml gelatin, 0.45% NP40, 0.45% Tween 20) and frozen until use. When PCR is to be performed, 0.6 µl of proteinase K (2 mg/ml) is added to the cells in the PCR lysis buffer. The sample is then heated to about 60° C. and incubated for 1 hr. Digestion is stopped through inactivation of the proteinase K by heating the samples to 95° C. for 10 min and then cooling on ice.

A relatively easy procedure for extracting DNA for PCR is a salting out procedure adapted from the method described by Miller et al., Nucleic Acids Res. 16:1215 (1988), which is incorporated herein by reference. Mononuclear cells are separated on a Ficoll-Hypaque gradient. The cells are resuspended in 3 ml of lysis buffer (10 mM Tris-HCl, 400 mM NaCl, 2 mM $Na_2$ EDTA, pH 8.2). Fifty µl of a 20 mg/ml solution of proteinase K and 150 µl of a 20% SDS solution are added to the cells and then incubated at 37° C. overnight. Rocking the tubes during incubation will improve the digestion of the sample. If the proteinase K digestion is incomplete after overnight incubation (fragments are still visible), an additional 50 µl of the 20 mg/ml proteinase K solution is mixed in the solution and incubated for another night at 37° C. on a gently rocking or rotating platform. Following adequate digestion, one ml of a 6M NaCl solution is added to the sample and vigorously mixed. The resulting solution is centrifuged for 15 minutes at 3000 rpm. The pellet contains the precipitated cellular proteins, while the supernatant contains the DNA. The supernatant is removed to a 15 ml tube that contains 4 ml of isopropanol. The contents of the tube are mixed gently until the water and the alcohol phases have mixed and a white DNA precipitate has formed. The DNA precipitate is removed and dipped in a solution of 70% ethanol and gently mixed. The DNA precipitate is removed from the ethanol and air-dried. The precipitate is placed in distilled water and dissolved.

Kits for the extraction of high-molecular weight DNA for PCR include a Genomic Isolation Kit A.S.A.P. (Boehringer Mannheim, Indianapolis, Ind.), Genomic DNA Isolation System (GIBCO BRL, Gaithersburg, Md.), Elu-Quik DNA Purification Kit (Schleicher & Schuell, Keene, N.H.), DNA Extraction Kit (Stratagene, LaJolla, Calif.), TurboGen Isolation Kit (Invitrogen, San Diego, Calif.), and the like. Use of these kits according to the manufacturer's instructions is generally acceptable for purification of DNA prior to practicing the methods of the present invention.

The concentration and purity of the extracted DNA can be determined by spectrophotometric analysis of the absorbance of a diluted aliquot at 260 nm and 280 nm. After extraction of the DNA, PCR amplification may proceed. The first step of each cycle of the PCR involves the separation of the nucleic acid duplex formed by the primer extension. Once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid.

In a particularly useful embodiment of PCR amplification, strand separation is achieved by heating the reaction to a sufficiently high temperature for a sufficient time to cause the denaturation of the duplex but not to cause an irreversible denaturation of the polymerase (see U.S. Pat. No. 4,965,188, incorporated herein by reference). Typical heat denaturation involves temperatures ranging from about 80° C. to 105° C. for times ranging from seconds to minutes. Strand separation, however, can be accomplished by any suitable denaturing method including physical, chemical, or enzymatic means. Strand separation may be induced by a helicase, for example, or an enzyme capable of exhibiting helicase activity. For example, the enzyme RecA has helicase activity in the presence of ATP. The reaction conditions suitable for strand separation by helicases are known in the art (see Kuhn Hoffman-Berling, 1978, CSH-Quantitative Biology, 43:63–67; and Radding, 1982, Ann. Rev. Genetics 16:405–436, each of which is incorporated herein by reference).

Template-dependent extension of primers in PCR is catalyzed by a polymerizing agent in the presence of adequate amounts of four deoxyribonucleotide triphosphates (typically DATP, dGTP, dCTP, and dTTP) in a reaction medium comprised of the appropriate salts, metal cations, and pH buffering systems. Suitable polymerizing agents are enzymes known to catalyze template-dependent DNA synthesis. In some cases, the target regions may encode at least a portion of a protein expressed by the cell. In this instance, mRNA may be used for amplification of the target region. Alternatively, PCR can be used to generate a cDNA library from RNA for further amplification, the initial template for primer extension is RNA. Polymerizing agents suitable for synthesizing a complementary, copy-DNA (cDNA) sequence from the RNA template are reverse transcriptase (RT), such as avian myeloblastosis virus RT, Moloney murine leukemia virus RT, or Thermus thermophilus (Tth) DNA polymerase, a thermostable DNA polymerase with reverse transcriptase activity marketed by Perkin Elmer Cetus, Inc. Typically, the genomic RNA template is heat degraded during the first denaturation step after the initial reverse transcription step leaving only DNA template. Suitable polymerases for use with a DNA template include, for example, *E. coli* DNA polymerase I or its Klenow fragment, T4 DNA polymerase, Tth polymerase, and Taq polymerase, a heat-stable DNA polymerase isolated from Thermus aquaticus and commercially available from Perkin Elmer Cetus, Inc. The latter enzyme is widely used in the amplification and sequencing of nucleic acids. The reaction conditions for using Taq polymerase are known in the art and are described in Gelfand, 1989, PCR Technology, supra.

Allele Specific PCR

Allele-specific PCR differentiates between target regions differing in the presence of absence of a variation or polymorphism. PCR amplification primers are chosen which bind only to certain alleles of the target sequence. This method is described by Gibbs, Nucleic Acid Res. 17:12427–2448 (1989).

Allele Specific Oligonucleotide Screening Methods

Further diagnostic screening methods employ the allele-specific oligonucleotide (ASO) screening methods, as described by Saiki et al., Nature 324:163–166 (1986). Oligonucleotides with one or more base pair mismatches are generated for any particular allele. ASO screening methods detect mismatches between variant target genomic or PCR amplified DNA and non-mutant oligonucleotides, showing decreased binding of the oligonucleotide relative to a mutant oligonucleotide. Oligonucleotide probes can be designed that under low stringency will bind to both polymorphic forms of the allele, but which at high stringency, bind to the allele to which they correspond. Alternatively, stringency conditions can be devised in which an essentially binary response is obtained, i.e., an ASO corresponding to a variant form of the target gene will hybridize to that allele, and not to the wildtype allele.

Ligase Mediated Allele Detection Method

Target regions of a test subject's DNA can be compared with target regions in unaffected and affected family members by ligase-mediated allele detection. See Landegren et al., Science 241:107–1080 (1988). Ligase may also be used to detect point mutations in the ligation amplification reaction described in Wu et al., Genomics 4:560–569 (1989). The ligation amplification reaction (LAR) utilizes amplification of specific DNA sequence using sequential rounds of template dependent ligation as described in Wu, supra, and Barany, Proc. Nat. Acad. Sci. 88:189–193 (1990).

Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. DNA molecules melt in segments, termed melting domains, under conditions of increased temperature or denaturation. Each melting domain melts cooperatively at a distinct, base-specific melting temperature (TM). Melting domains are at least 20 base pairs in length, and may be up to several hundred base pairs in length.

Differentiation between alleles based on sequence specific melting domain differences can be assessed using polyacrylamide gel electrophoresis, as described in Chapter 7 of Erlich, ed., PCR Technology, Principles and Applications for DNA Amplification, W. H. Freeman and Co., New York (1992), the contents of which are hereby incorporated by reference.

Generally, a target region to be analyzed by denaturing gradient gel electrophoresis is amplified using PCR primers flanking the target region. The amplified PCR product is applied to a polyacrylamide gel with a linear denaturing gradient as described in Myers et al., Meth. Enzymol. 155:501–527 (1986), and Myers et al., in Genomic Analysis, A Practical Approach, K. Davies Ed. IRL Press Limited, Oxford, pp. 95–139 (1988), the contents of which are hereby incorporated by reference. The electrophoresis system is maintained at a temperature slightly below the Tm of the melting domains of the target sequences.

In an alternative method of denaturing gradient gel electrophoresis, the target sequences may be initially attached to a stretch of GC nucleotides, termed a GC clamp, as described in Chapter 7 of Erlich, supra. Preferably, at least 80% of the nucleotides in the GC clamp are either guanine or cytosine. Preferably, the GC clamp is at least 30 bases long. This method is particularly suited to target sequences with high Tm's.

Generally, the target region is amplified by the polymerase chain reaction as described above. One of the oligonucleotide PCR primers carries at its 5' end, the GC clamp region, at least 30 bases of the GC rich sequence, which is incorporated into the 5' end of the target region during amplification. The resulting amplified target region is run on an electrophoresis gel under denaturing gradient conditions as described above. DNA fragments differing by a single base change will migrate through the gel to different positions, which may be visualized by ethidium bromide staining.

Temperature Gradient Gel Electrophoresis

Temperature gradient gel electrophoresis (TGGE) is based on the same underlying principles as denaturing gradient gel electrophoresis, except the denaturing gradient is produced by differences in temperature instead of differences in the concentration of a chemical denaturant. Standard TGGE utilizes an electrophoresis apparatus with a temperature gradient running along the electrophoresis path. As samples migrate through a gel with a uniform concentration of a chemical denaturant, they encounter increasing temperatures. An alternative method of TGGE, temporal temperature gradient gel electrophoresis (TTGE or tTGGE) uses a steadily increasing temperature of the entire electrophoresis gel to achieve the same result. As the samples migrate through the gel the temperature of the entire gel increases, leading the samples to encounter increasing temperature as they migrate through the gel. Preparation of samples, including PCR amplification with incorporation of a GC clamp, and visualization of products are the same as for denaturing gradient gel electrophoresis.

Single-Strand Conformation Polymorphism Analysis

Target sequences or alleles at an HMGA locus can be differentiated using single-strand conformation polymorphism analysis, which identifies base differences by alteration in electrophoretic migration of single stranded PCR products, as described in Orita et al., Proc. Nat. Acad. Sci. 85:2766–2770 (1989). Amplified PCR products can be generated as described above, and heated or otherwise denatured, to form single stranded amplification products. Single-stranded nucleic acids may refold or form secondary structures which are partially dependent on the base sequence. Thus, electrophoretic mobility of single-stranded amplification products can detect base-sequence difference between alleles or target sequences.

Chemical or Enzymatic Cleavage of Mismatches

Differences between target sequences can also be detected by differential chemical cleavage of mismatched base pairs, as described in Grompe et al., Am. J. Hum. Genet. 48:212–222 (1991). In another method, differences between target sequences can be detected by enzymatic cleavage of mismatched base pairs, as described in Nelson et al., Nature Genetics 4:11–18 (1993). Briefly, genetic material from an animal and an affected family member may be used to generate mismatch free heterohybrid DNA duplexes. As used herein, "heterohybrid" means a DNA duplex strand comprising one strand of DNA from one animal, and a second DNA strand from another animal, usually an animal differing in the phenotype for the trait of interest. Positive selection for heterohybrids free of mismatches allows determination of small insertions, deletions or other polymorphisms that may be associated with HMGA polymorphisms.

Non-gel Systems

Other possible techniques include non-gel systems such as TaqMan™ (Perkin Elmer). In this system oligonucleotide PCR primers are designed that flank the mutation in question and allow PCR amplification of the region. A third oligonucleotide probe is then designed to hybridize to the region containing the base subject to change between different alleles of the gene. This probe is labeled with fluorescent dyes at both the 5' and 3' ends. These dyes are chosen such that while in this proximity to each other the fluorescence of one of them is quenched by the other and cannot be detected. Extension by Taq DNA polymerase from the PCR primer positioned 5' on the template relative to the probe leads to the cleavage of the dye attached to the 5' end of the annealed probe through the 5' nuclease activity of the Taq DNA polymerase. This removes the quenching effect allowing detection of the fluorescence from the dye at the 3' end of the probe. The discrimination between different DNA sequences arises through the fact that if the hybridization of the probe to the template molecule is not complete, i.e. there is a mismatch of some form, the cleavage of the dye does not take place. Thus only if the nucleotide sequence of the oligonucleotide probe is completely complimentary to the template molecule to which it is bound will quenching be removed. A reaction mix can contain two different probe sequences each designed against different alleles that might be present thus allowing the detection of both alleles in one reaction.

Yet another technique includes an Invader Assay which includes isothermic amplification that relies on a catalytic release of fluorescence. See Third Wave Technology at www.twt.com.

Non-PCR Based DNA Diagnostics

The identification of a DNA sequence linked to an HMGA sequence can be made without an amplification step, based on polymorphisms including restriction fragment length polymorphisms in an animal and a family member. Hybridization probes are generally oligonucleotides which bind through complementary base pairing to all or part of a target nucleic acid. Probes typically bind target sequences lacking complete complementarity with the probe sequence depending on the stringency of the hybridization conditions. The probes are preferably labeled directly or indirectly, such that by assaying for the presence or absence of the probe, one can detect the presence or absence of the target sequence. Direct labeling methods include radioisotope labeling, such as with 32P or 35S. Indirect labeling methods include fluorescent tags, biotin complexes which may be bound to avidin or streptavidin, or peptide or protein tags. Visual detection methods include photoluminescents, Texas red, rhodamine and its derivatives, red leuco dye and 3,3',5,5'-tetramethylbenzidine (TMB), fluorescein, and its derivatives, dansyl, umbelliferone and the like or with horse radish peroxidase, alkaline phosphatase and the like.

Hybridization probes include any nucleotide sequence capable of hybridizing to a porcine chromosome where one of the HMGA encoding sequence resides, and thus defining a genetic marker linked to one of the HMGA genes, including a restriction fragment length polymorphism, a hypervariable region, repetitive element, or a variable number tandem repeat. Hybridization probes can be any gene or a suitable analog. Further suitable hybridization probes include exon fragments or portions of cDNAs or genes known to map to the relevant region of the chromosome.

Preferred tandem repeat hybridization probes for use according to the present invention are those that recognize a small number of fragments at a specific locus at high stringency hybridization conditions, or that recognize a larger number of fragments at that locus when the stringency conditions are lowered.

One or more additional restriction enzymes and/or probes and/or primers can be used. Additional enzymes, constructed probes, and primers can be determined by routine experimentation by those of ordinary skill in the art and are intended to be within the scope of the invention.

Although the methods described herein may be in terms of the use of a single restriction enzyme and a single set of primers, the methods are not so limited. One or more additional restriction enzymes and/or probes and/or primers can be used, if desired. Indeed in some situations it may be preferable to use combinations of markers giving specific haplotypes. Additional enzymes, constructed probes and primers can be determined through routine experimentation, combined with the teachings provided and incorporated herein.

According to the invention, polymorphisms in one or both of the HMGA nucleotide sequences have been identified which have an association with growth, fatness, meat quality, and feed efficiency. The presence or absence of the markers, in one embodiment may be assayed by PCR RFLP analysis using the restriction endonucleases and amplification primers may be designed using analogous human, pig or other of the HMGA sequences due to the high homology in the region surrounding the polymorphisms, or may be designed using known HMGA sequences (for example, human) as exemplified in GenBank or even designed from sequences obtained from linkage data from closely surrounding genes based upon the teachings and references herein. The sequences surrounding the polymorphism will facilitate the development of alternate PCR tests in which a primer of about 4–30 contiguous bases taken from the sequence immediately adjacent to the polymorphism is used in connection with a polymerase chain reaction to greatly amplify the region before treatment with the desired restriction enzyme. The primers need not be the exact complement; substantially equivalent sequences are acceptable. The design of primers for amplification by PCR is known to those of skill in the art and is discussed in detail in Ausubel (ed.), "Short Protocols in Molecular Biology, Fourth Edition" John Wiley and Sons 1999. The following is a brief description of primer design.

Primer Design Strategy

Increased use of polymerase chain reaction (PCR) methods has stimulated the development of many programs to aid in the design or selection of oligonucleotides used as primers for PCR. Four examples of such programs that are freely available via the Internet are: PRIMER by Mark Daly and Steve Lincoln of the Whitehead Institute (UNIX, VMS, DOS, and Macintosh), Oligonucleotide Selection Program (OSP) by Phil Green and LaDeana Hiller of Washington University in St. Louis (UNIX, VMS, DOS, and Macintosh), PGEN by Yoshi (DOS only), and Amplify by Bill Engels of the University of Wisconsin (Macintosh only). Generally these programs help in the design of PCR primers by searching for bits of known repeated-sequence elements and then optimizing the $T_m$ by analyzing the length and GC content of a putative primer. Commercial software is also available and primer selection procedures are rapidly being included in most general sequence analysis packages.

Sequencing and PCR Primers

Designing oligonucleotides for use as either sequencing or PCR primers requires selection of an appropriate sequence that specifically recognizes the target, and then testing the sequence to eliminate the possibility that the oligonucleotide will have a stable secondary structure. Inverted repeats in the sequence can be identified using a repeat-identification or RNA-folding program such as those described above (see prediction of Nucleic Acid Structure). If a possible stem structure is observed, the sequence of the primer can be shifted a few nucleotides in either direction to minimize the predicted secondary structure. The sequence of the oligonucleotide should also be compared with the sequences of both strands of the appropriate vector and insert DNA. Obviously, a sequencing primer should only have a single match to the target DNA. It is also advisable to exclude primers that have only a single mismatch with an undesired target DNA sequence. For PCR primers used to amplify genomic DNA, the primer sequence should be compared to the sequences in the GenBank database to determine if any significant matches occur. If the oligonucleotide sequence is present in any known DNA sequence or, more importantly, in any known repetitive elements, the primer sequence should be changed.

The methods and materials of the invention may also be used more generally to evaluate animal DNA, genetically type individual animals, and detect genetic differences in animals. In particular, a sample of animal genomic DNA may be evaluated by reference to one or more controls to determine if a polymorphism in one of the HMGA sequences is present. Preferably, RFLP analysis is performed with respect to the animal's HMGA sequences, and the results are compared with a control. The control is the result of a RFLP analysis of one or both of the HMGA sequences of a different animal where the polymorphism of the animal HMGA genes is known. Similarly, the HMGA genotype of a animal may be determined by obtaining a sample of its genomic DNA, conducting RFLP analysis of the HMGA genes in the DNA, and comparing the results with a control. Again, the control is the result of RFLP analysis of one of the HMGA sequences of a different animal. The results genetically type the animal by specifying the polymorphism(s) in its HMGA genes. Finally, genetic differences among animals can be detected by obtaining samples of the genomic DNA from at least two animals, identifying the presence or absence of a polymorphism in one of the HMGA nucleotide sequences, and comparing the results.

These assays are useful for identifying the genetic markers relating to growth, fatness, meat quality, and feed efficiency, as discussed above, for identifying other polymorphisms in the HMGA genes that may be correlated with other characteristics, and for the general scientific analysis of animal genotypes and phenotypes.

The examples and methods herein disclose certain genes which have been identified to have a polymorphism which is associated either positively or negatively with a beneficial trait that will have an effect on growth, fatness, meat quality, and feed efficiency for animals carrying this polymorphism. The identification of the existence of a polymorphism within a gene is often made by a single base alternative that results in a restriction site in certain allelic forms. A certain allele, however, as demonstrated and discussed herein, may have a number of base changes associated with it that could be assayed for which are indicative of the same polymorphism (allele). Further, other genetic markers or genes may be linked to the polymorphisms disclosed herein so that assays may involve identification of other genes or gene fragments, but which ultimately rely upon genetic characterization of animals for the same polymorphism. Any assay which sorts and identifies animals based upon the allelic differences disclosed herein are intended to be included within the scope of this invention.

One of skill in the art, once a polymorphism has been identified and a correlation to a particular trait established, will understand that there are many ways to genotype animals for this polymorphism. The design of such alternative tests merely represent optimization of parameters known to those of skill in the art and are intended to be within the scope of this invention as fully described herein.

EXAMPLES

The HMGI (HMGA under a new nomenclature; Bustin, 2001) gene family consists of two genes that encode three proteins (HMG-I, -Y, and -C) associated with chromatin structure and control of transcription. The HMGI/Y proteins are products of alternatively spliced RNA of a single gene, but a different gene encodes HMGIC.

The HMGIY (HMGA1) gene is located at chromosomal region 6p21 in humans (Friedmann et al., 1993) and may be involved in the regulation of gene expression for cell growth and differentiation (Reeves and Beckerbauer, 2001). Therefore, aberrant or over-expression of the HMGI/Y protein has been strongly correlated with many types of cancer formation (Hess, 1998; Tallini and Dal Cin, 1999; Reeves, 2000). As the HMGI/Y proteins play a transcriptional role in the expression of adipocyte-specific genes, the HMGI/Y might have an important role in adipocytic cell growth and differentiation (Melillo et al., 2001).

The human HMGIC (HMGA2) gene was physically assigned to chromosome 12q14-12 and this region was shown for a site of chromosomal rearrangements that frequently cause lipomas, a tumor mainly composed of mature fat cells (Asher et al., 1995). These findings were confirmed in transgenic mice expressing truncated domains of the HMGIC gene. These transgenic mice developed adiposity and abnormally high prevalence of lipomas (Arlotta et al., 2000). Otherwise, the HMGIC gene knockout mice showed a reduction of the adult body weight, mainly affecting fat tissue (Zhou et al., 1995). These results indicate that variation in HMGA genes might be associated with variation in human obesity and fatness in animals.

HMGA1: PCR-RFLP Tests

Primers:
Forward (HMGY1)-5' AGA AGG AGC CCA GCG AAG T 3' SEQ ID NO:1
Reverse (HMYS2)-5' ACA GTG CTC ACC CAA TGG C 3' SEQ ID NO:2
Locations: Both in exon PCR Conditions:
Mix 1

| | |
|---|---|
| 10 × PCR Buffer | 1.0 µl |
| $MgCl_2$ (25 mM) | 0.6 µl |
| dNTPs (2.5 mM) | 0.5 µl |
| HMGY1 (25 pmol/µl) | 0.1 µl |
| HMYS 2 (25 pmol/µl) | 0.1 µl |
| Taq Polymerase (5 U/µl) | 0.07 µl |
| dd$H_2$O | 7.63 µl |
| genomic DNA | 1.0 µl |

Combine the Mix 1 and DNA in a PCR reaction tube. Overlay mix with mineral oil. Run the following PCR program: 94° C. for 3 min; 36 cycles of 94° C. for 30 sec, 63.8° C. for 1 min, and 72° C. for 1 min 30 sec; followed by a final extension at 72° C. for 10 min. Check 2 µl of the PCR on a 1.6% agarose gel to confirm amplification success and the desirable clean result in the negative control.

Digestion can be Performed by the Following Procedures:

| BanI digestion reaction: | | NaeI digestion reaction: | |
|---|---|---|---|
| PCR product | 4.0 μl | PCR product | 4.0 μl |
| NE Buffer 4 | 1.0 μl | NE Buffer 1 | 1.0 μl |
| BSA (10 mg/ml) | 0.1 μl | BSA (10 mg/ml) | 0.1 μl |
| BanI (20 U/μl) | 0.2 μl | NaeI (10 U/μl) | 0.4 μl |
| ddH$_2$O | 4.7 μl | ddH$_2$O | 4.5 μl |

Make a cocktail of the PCR product, buffer, enzyme and water. Incubate for at least 4 hours or overnight at 37° C. Mix the digest with loading dye (2:5) and run on a 3% NuSieve agarose gel.

HMGA2: HhaI PCR-RFLP Tests

Primers for HMGIC-5: 5' ACT GAA GAG ACA TCC TCA CA 3' SEQ ID NO:3
HMGIC-T1: 5' CTA AAC CTG GGA CTG TGA AG 3' SEQ ID NO:4

Primers for Mix 2: 660 bp

HMGIC-SF:
5' GAT AGG ACT AGA TAC AAC TTA C 3'     SEQ ID NO:5

HMGIC-T2:
5' GGA TAT ATT GCA TCT CTG GC 3'     SEQ ID NO:6

Mix 1: 250 bp

PCR Conditions:

| | Mix 1: | | Mix 2: | |
|---|---|---|---|---|
| 10 × Promega Buffer | 1.0 μL | 10 × Promega Buffer | 1.0 μL |
| 25 mM MgCl$_2$ | 0.6 μL | 25 mM MgCl$_2$ | 0.6 μL |
| dNTPs mix (2.5 mM each) | 0.5 μL | dNTPs mix (2.5 mM each) | 0.5 μL |
| 25 pmol/μL HMGIC 5 | 0.1 μL | 25 pmol/μL HMGIC SF | 0.1 μL |
| 25 pmol/μL HMGIC T1 | 0.1 μL | 25 pmol/μL HMGIC T2 | 0.1 μL |
| dd sterile H$_2$0 | 7.4 μL | dd sterile H$_2$0 | 7.4 μL |
| Taq Polymerase (5 U/μL) | 0.07 μL | Taq Polymerase (5 U/μL) | 0.07 μL |
| genomic DNA (12.5 ng/μL) | 1.0 μL | genomic DNA (12.5 ng/μL) | 1.0 μL |

1. Run the following PCR program: 94° C. for 2 min; 35 cycles of 94° C. for 30 sec, 56° C. (Mix 1) and 52° C. (Mix 2) 1 min, and 72° C. 1 min 30 sec; followed by a final extension at 72° C. for 10 min. When HMGIC-5 and HMGIC-T2 primers are used for PCR amplification (56° C. annealing temp.), the PCR fragment (1.2 kb) contains both HhaI polymorphic sites.
2. Check 3 μL of the PCR reaction on a standard 1% agarose gel to confirm amplification success and clean negative control.
3. HhaI Digestion Reaction: Add 5 μL to each reaction tube containing the DNA. Incubate at 37° C. at least 4 hours to overnight. Mix loading dye with digestion reaction and load the total volume on a 3% agarose gel.

| | |
|---|---|
| PCR product | 5.0 μl |
| 10 × NE Buffer 4 | 1.0 μL |
| BSA (10 mg/ml) | 0.3 μL |
| HhaI enzyme (20 U/μL) | 0.3 μL |
| dd sterile H$_2$0 | 3.6 μL |

FIG. 1 BanI recognition site are indicated as underlined and bold. One of which contains the single nucleotide polymorphism at position 54.

FIG. 1 shows the HMGA sequence with the NaeI polymorphic site (GCYGGC) underlined.

Y=C or T

In FIG. 2 three HhaI recognition (GCGC) sites are underlined and two of them highlighted with gray contain DNA polymorphism Box 1 is approximate PCR fragment of the Mix 1.
Box 2 is approximate PCR fragment of the Mix 2.

K=G or T

Y=C or T

We sequenced and analyzed both porcine HMGA1 and HMGA2 fragments amplified from polymerase chain reaction The sequence of the porcine HMGA2 gene fragment, spanning exon 5 and 3' UTR showed about 79% identity at the DNA level to corresponding human sequence. The sequence of the porcine HMGA1 gene fragment, spanning exon 6 and 7 showed about 93% identity at the DNA level to the corresponding human exonic sequence.

We identified several single nucleotide substitutions (SNPs) in both porcine HMGA1 and HMGA2 genes. Two SNPs identified in the HMGA1 gene were situated within restriction enzyme recognition sites, BanI and NaeI, respectively and another two SNPs identified in the HMGA2 gene were situated at the HhaI recognition site. PCR RFLP tests for these SNPs were developed and tested for DNA samples from animals of Berkshire×Yorkshire 3 generation family and PIC commercial populations. QTL and association analyses were performed using genotypes from the PCR-RFLP tests in the DNA samples mentioned above. Both HMGA genes are located under QTL regions for fat related traits in Berkshire and Yorkshire crossed reference family. The presence of allele 1 NaeI polymorphism for HMGA1 gene is significantly associated with less backfat in animals from several commercial populations of PIC. In addition, the HMGA2 genotypes are also associated with fat and growth traits in those commercial populations. Combined analyses of both genes in the reference family clearly show additive effects of two genes on the fat traits.

These results indicate that these polymorphsims were associated with many economically important traits for pig production and pork quality and further use of these polymorphisms will be useful for accurate selection of animals with desirable performance and phenotypes for breeding program.

Association Analyses of HMGA Genes in PIC Populations

Mean (s.e.) and sigma P are calculated on all animals in the meat quality file on Aug. 1, 2000.

All results are from mixed model with sire as random effect and slaughterdate as fixed.

LSmeans significance levels: α and δ significance levels:

| | | | |
|---|---|---|---|
| a–b | p < .3 | a | p < .3 |
| c–d | p < .1 | b | p < .1 |
| e–f | p < .05 | c | p < .05 |
| g–h | p < .01 | d | p < .01 |
| i–j | p < .005 | e | p < .005 |
| k–l | p < .001 | f | p < .001 |
| m–n | p < .0005 | g | p < .0005 |
| o–p | p < .0001 | h | p < .0001 |

—B— Estimate is biased.

geno p: p value for genotype in the model TRAIT=Sire+ Slaughterdate +Genotype expl. %σe2 reduction in error variance due to "Genotype".

α and β additive and dominance effect of the marker from model TRAIT=Sire+Sl.date+ADD+DOM results are given in trait values.

| Trait | Description |
|---|---|
| dirty wt | Dirty weight of the carcass |
| hcw | Weight of the hot carcass |
| ccw | Weight of the cold carcass |
| L_binwt | bone in weight of the loin (one loin) |
| L_blswt | boneless weight of the loin (one loin) |
| loinminl | minolta L objective color score of the loin |
| loinmina | minolta a objective color score of the loin |
| loinminb | minolta b objective color score of the loin |
| japcs | Subjective measure: japanese color score (1–6) |
| marbling | Subjective score of marbling in the loin (1–5) |
| firmness | Subjective score of loin firmness (1–3) |
| loinpH | loin pH at 24 hours |
| h_binwt | bone in weight of the ham (one ham) |
| h_blswt | boneless weight of the inside muscle of the ham (one ham) |
| hamminl | minolta L objective color score of the ham |
| hammina | minolta a objective color score of the ham |
| hamminb | minolta b objective color score of the ham |
| hampH | ham pH at 24 hours |
| dripprct | Percentage driploss (reduction of the weight of the sample) after 48 hours |
| hprofat | Henessey probe backfat thickness |
| hpromeat | Henessey probe loin depth |
| hprorib | Henessey probe rib thickness |
| LMprct | Lean meat percentage of the carcass |
| aloc_f | Aloca backfat thickness P2 position |
| endwt | weight of the animal at the end of test |
| days | days until the end of test period |
| LDG, g/d | life time daily gain (from birth to end of test period) |
| TDG, g/d | daily gain while on test |
| US_MD | muscle depth at end of test period |

Analysis of meat quality and production traits with HMGA1 Nae I in US-Landrace.

| Trait | Mean (s.e.) | $\sigma_p$ | No. animals 11 | 12 | 22 | LSmeans (s.e.) 11 | 12 | 22 | geno p | α trait (s.e.) | p | δ trait (s.e.) | p |
|---|---|---|---|---|---|---|---|---|---|---|---|---|---|
| marbling | 1.72 (0.03) | 0.62 | 170 | 184 | 38 | 1.73 (0.04)a | 1.75 (0.05)c | 1.60 (0.09)b d | 0.20 | −0.07 (0.05) | a | 0.06 (0.04) | a |
| firmness | 2.75 (0.07) | 1.13 | 123 | 108 | 14 | 2.81 (0.07)e | 2.99 (0.07)f | 2.90 (0.17) | 0.06 | 0.05 (0.09) | | 0.09 (0.07) | a |
| dripprct | 2.80 (0.09) | 1.44 | 128 | 111 | 13 | 2.55 (0.14)a c | 2.82 (0.15)bg | 1.79 (0.38)d h | 0.02 | −0.38 (0.20) | b | 0.43 (0.16) | d |
| hprofat | 12.98 (0.11) | 2.51 | 215 | 219 | 45 | 12.77 (0.21)e | 13.40 (0.22)f | 13.77 (0.41)f | 0.014 | 0.50 (0.22) | c | 0.09 (0.17) | |
| Hpromeat | 53.08 (0.57) | 12.7 | 220 | 227 | 51 | 53.41 (0.64)e | 53.46 (0.67)e | 56.15 (1.15)f | 0.04 | 1.37 (0.59) | c | −0.88 (0.47) | b |
| Hprorib | 13.20 (0.25) | 3.9 | 124 | 109 | 17 | 13.35 (0.39)i c | 11.89 (0.44)j | 11.59 (0.96)d | 0.008 | −0.88 (0.50) | b | −0.38 (0.40) | |
| LMprct | 46.77 (0.08) | 1.16 | 119 | 101 | 11 | 46.99 (0.14)e a | 46.67 (0.16)f | 46.52 (0.36)b | 0.10 | −0.23 (0.18) | a | −0.06 (0.14) | |
| Days | 159.1 (0.70) | 12.1 | 136 | 128 | 34 | 156.4 (0.82)a i | 157.6 (0.87)bg | 162.1 (1.60)j h | 0.005 | 2.84 (0.87) | e | −1.14 (0.74) | a |
| US_MD | 60.75 (0.38) | 7.71 | 173 | 195 | 48 | 60.53 (0.62)c | 60.68 (0.61)c | 62.87 (1.10) d | 0.12 | 1.17 (0.60) | b | −0.68 (0.50) | a |

Analysis of meat quality and production traits with HMGA1 Nae I in US-Large White

| Trait | Mean (s.e.) | $\sigma_p$ | No. animals 11 | 12 | 22 | LSmeans (s.e.) 11 | 12 | 22 | geno p | α trait (s.e.) | p | δ trait (s.e.) | p |
|---|---|---|---|---|---|---|---|---|---|---|---|---|---|
| HcW | 188.5 (0.78) | 14.5 | 93 | 162 | 87 | 185.9 (1.83)c e | 189.2 (1.47)d | 190.4 (1.75)f | 0.09 | 2.26 (1.08) | c | 0.71 (0.98) | |
| Ccw | 186.3 (0.82) | 14.5 | 82 | 150 | 78 | 183.6 (1.88)c e | 187.0 (1.52)d | 188.4 (1.79)f | 0.08 | 2.39 (1.13) | c | 0.70 (0.99) | |
| Dripprct | 2.30 (0.11) | 1.2 | 30 | 62 | 28 | 2.67 (0.30) e | 2.47 (0.22)e | 1.86 (0.28) f | 0.07 | −0.41 (0.18) | c | 0.14 (0.16) | |
| Hprofat | 14.09 (0.15) | 2.61 | 86 | 150 | 79 | 13.66 (0.39)a i | 14.12 (0.32)be | 14.95 (0.37) f | 0.012 | 0.65 (0.22) | e | −0.12 (0.19) | |
| Hprorib | 13.46 (0.37) | 3.97 | 33 | 58 | 23 | 12.93 (0.98) e | 13.49 (0.76)e | 15.81 (0.99) f | 0.06 | 1.44 (0.61) | c | −0.58 (0.54) | a |
| LMprct | 46.09 (0.10) | 0.96 | 28 | 48 | 20 | 46.39 (0.27) c | 46.25 (0.21)c | 45.72 (0.27) d | 0.13 | −0.33 (0.15) | b | 0.13 (0.15) | |
| aloc_f | 13.48 (0.17) | 3.2 | 98 | 170 | 90 | 12.95 (0.41)a c | 13.42 (0.32)be | 14.40 (0.39) f | 0.009 | 0.73 (0.24) | e | −0.17 (0.22) | |
| Endwt | 109.5 (0.36) | 6.84 | 98 | 170 | 90 | 107.7 (0.90)a c | 109.1 (0.72)b | 109.5 (0.87) d | 0.17 | 0.91 (0.52) | b | 0.33 (0.47) | |
| Days | 170.2 (0.78) | 10.6 | 43 | 82 | 58 | 166.2 (1.89)a e | 163.8 (1.48)b | 161.9 (1.65) f a | 0.09 | −2.17 (0.98) | c | −0.20 (0.93) | |
| US_MD | 58.71 (0.38) | 6.92 | 96 | 160 | 82 | 57.60 (0.74)a i | 58.66 (0.59)be | 60.64 (0.75)j f | 0.009 | 1.52 (0.50) | e | −0.31 (0.45) | |

Analysis of meat quality and production traits with HMGA1 Nae I in US-Large White × Duroc

| Trait | Mean (s.e.) | $\sigma_P$ | No. animals 11 | 12 | 22 | LSmeans (s.e.) 11 | 12 | 22 | geno p | α trait (s.e.) | p | δ trait (s.e.) | p |
|---|---|---|---|---|---|---|---|---|---|---|---|---|---|
| Hprofat | 15.88 (0.16) | 3.46 | 128 | 245 | 109 | 15.41 (0.37) c | 15.45 (0.29) e | 16.31 (0.39)d f | 0.06 | 0.45 (0.23) | b | −0.28 (0.19) | a |
| aloc_f | 13.83 (0.15) | 3.47 | 148 | 274 | 119 | 13.35 (0.32)c i | 13.98 (0.26)d | 14.68 (0.36)j c | 0.010 | 0.67 (0.22) | e | −0.02 (0.18) | |

Analysis of meat quality and production traits with HMGA1 Nae I Across All lines

| Trait | Mean (s.e.) | $\sigma_P$ | No. animals 11 | 12 | 22 | LSmeans (s.e.) 11 | 12 | 22 |
|---|---|---|---|---|---|---|---|---|
| Loinmina | 6.85 (0.03) | 1.59 | 634 | 853 | 702 | 6.90 (0.09) c | 7.05 (0.08)d | 7.08 (0.07)d |
| Loinminb | 3.36 (0.03) | 1.3 | 627 | 841 | 695 | 3.37 (0.06)a e | 3.44 (0.05)b | 3.53 (0.05)f a |
| HampH | 5.70 (0.00) | 0.18 | 398 | 529 | 475 | 5.71 (0.01)e | 5.69 (0.01)f a | 5.70 (0.01) b |
| Hprofat | 14.68 (0.09) | 4.17 | 594 | 791 | 680 | 15.42 (0.20)a i | 15.66 (0.17)b e | 16.06 (0.16)j f |
| Hpromeat | 54.16 (0.28) | 12.9 | 612 | 826 | 694 | 54.95 (0.47) e | 55.32 (0.40)c | 56.10 (0.37)f d |
| LMprct | 46.17 (0.06) | 2.01 | 313 | 388 | 353 | 45.98 (0.13)a e | 45.86 (0.11)b e | 45.60 (0.10) f |
| aloc_f | 13.23 (0.08) | 3.91 | 664 | 883 | 733 | 13.59 (0.20)c i | 13.90 (0.17)de | 14.28 (0.16)j f |
| US_MD | 59.04 (0.19) | 8.37 | 536 | 710 | 679 | 57.19 (0.45)a i | 57.77 (0.39)be | 58.71 (0.35)j f |

| Trait | geno p | Line* geno p | α trait (s.e.) | p | | δ trait (s.e.) | p | |
|---|---|---|---|---|---|---|---|---|
| Loinmina | 0.12 | 0.16 | 0.09 (0.05) | b | | 0.04 (0.04) | | |
| Loinminb | 0.09 | 0.003 | 0.08 (0.04) | c | b | −0.01 (0.03) | | c |
| HampH | 0.02 | 0.22 | −0.00 (0.01) | | | −0.01 (0.01) | c | |
| Hprofat | 0.02 | 0.12 | 0.32 (0.11) | e | b | −0.05 (0.09) | | b |
| Hpromeat | 0.10 | 0.72 | 0.58 (0.27) | c | | −0.14 (0.23) | | |
| LMprct | 0.04 | 0.47 | −0.19 (0.07) | c | | 0.04 (0.06) | a | |
| aloc_f | 0.008 | 0.45 | 0.34 (0.11) | e | a | −0.02 (0.09) | | |
| US_MD | 0.006 | 0.18 | 0.76 (0.24) | e | | −0.12 (0.20) | a | |

Analysis of meat quality and production traits with HMGA2 in US-Landrace.

| Trait | Mean (s.e.) | $\sigma_P$ | No. animals 11 | 12 | 22 | LSmeans (s.e.) 11 | 12 | 22 | geno p | α trait (s.e.) | p | δ trait (s.e.) | p |
|---|---|---|---|---|---|---|---|---|---|---|---|---|---|
| Hprofat | 12.96 (0.16) | 2.56 | 6 | 60 | 186 | 13.83 (0.99)a | 12.53 (0.37)be | 13.35 (0.27) f | 0.07 | −0.24 (0.49) | | −0.71 (0.39) | b |
| LMprct | 46.78 (0.08) | 1.17 | 5 | 51 | 135 | 46.07 (0.49)e a | 47.16 (0.19)fg | 46.67 (0.15)bh | 0.01 | 0.30 (0.24) | a | 0.53 (0.19) | d |
| Endwt | 111.6 (0.43) | 6.94 | 6 | 61 | 192 | 107.5 (2.81)c | 110.4 (0.96)e | 112.4 (0.68)d f | 0.04 | 2.48 (1.41) | b | 0.28 (1.11) | |
| LDG, g/d | 683.0 (2.98) | 48 | 6 | 61 | 192 | 638.0 (23.1)a | 661.8 (6.93)c | 674.2 (5.63)bd | 0.09 | 18.08 (11.5) | a | 3.78 (8.66) | |
| TDG, g/d | 896.1 (5.58) | 73.2 | 3 | 43 | 126 | 850.1 (41.0)a | 875.2 (12.1)e | 900.9 (9.76)b f | 0.08 | 25.41 (20.4) | a | −0.22 (15.4) | |

Analysis of meat quality and production traits with HMGA2 in US-Large White

| Trait | Mean (s.e.) | $\sigma_P$ | No. animals 11 | 12 | 22 | LSmeans (s.e.) 11 | 12 | 22 | geno p | α trait (s.e.) | p | δ trait (s.e.) | p |
|---|---|---|---|---|---|---|---|---|---|---|---|---|---|
| L_binwt | 19.78 (0.16) | 1.72 | 12 | 55 | 47 | 20.29 (0.45)e | 19.97 (0.25)e | 19.26 (0.26) f | 0.02 | −0.52 (0.23) | c | 0.13 (0.20) | |
| L_blswt | 6.68 (0.06) | 0.59 | 12 | 55 | 47 | 6.77 (0.15)c | 6.69 (0.09)e | 6.49 (0.09)d f | 0.08 | −0.14 (0.08) | b | 0.04 (0.07) | |
| Endwt | 109.9 (0.50) | 6.12 | 12 | 68 | 72 | 109.1 (1.85) | 109.4 (0.93)e | 107.2 (0.94) f | 0.12 | −0.94 (0.95) | | 0.80 (0.78) | |
| LDG, g/d | 662.4 (3.08) | 38 | 12 | 68 | 72 | 670.2 (11.2)a | 677.3 (5.89)i | 658.0 (5.21)b j | 0.009 | −6.12 (5.67) | a | 8.78 (4.63) | b |
| TDG, g/d | 863.5 (5.50) | 65.8 | 11 | 61 | 71 | 877.7 (19.3) a | 876.9 (9.85)g | 848.3 (8.78)b h | 0.02 | −14.7 (9.79) | a | 9.25 (8.00) | a |

Analysis of meat quality and production traits with HMGA2 in US-Duroc.

| Trait | Mean (s.e.) | $\sigma_p$ | No. animals | | | LSmeans (s.e.) | | | geno | α | | | δ | | |
|---|---|---|---|---|---|---|---|---|---|---|---|---|---|---|---|
| | | | 11 | 12 | 22 | 11 | 12 | 22 | p | trait (s.e.) | p | | trait (s.e.) | p | |
| dirty wt | 230.6 (1.65) | 19.1 | 50 | 48 | 36 | 227.6 (3.36)e | 227.8 (2.96)e | 236.0 (3.24)f | 0.07 | 4.20 (2.10) | c | | −2.68 (2.21) | a | |
| Hprofat | 13.49 (0.28) | 3.1 | 46 | 46 | 34 | 14.71 (0.67)i | c | 12.58 (0.59)j | 13.29 (0.64)d | 0.01 | −0.71 (0.39) | b | −0.94 (0.40) | c | |
| Endwt | 107.0 (0.86) | 9.97 | 50 | 49 | 35 | 104.6 (1.92)c | 104.7 (1.67)e | 109.1 (1.93)d f | 0.09 | 2.24 (1.17) | b | | −1.41 (1.20) | a | |
| LDG, g/d | 655.4 (4.65) | 53.9 | 50 | 49 | 35 | 648.1 (10.8)a | 636.5 (9.60)b e | 660.9 (10.9)b f | 0.09 | 6.40 (5.94) | a | | −12.0 (5.95) | c | |
| TDG, g/d | 847.4 (8.81) | 100 | 49 | 48 | 33 | 836.9 (19.4)a | 816.2 (17.0)e | 860.8 (19.5)b f | 0.09 | 11.95 (11.1) | a | | −21.8 (11.2) | b | |
| US_MD | 56.93 (0.60) | 6.94 | 50 | 49 | 35 | 55.01 (1.03)e c | 57.54 (0.91)f | 57.44 (1.05)d | 0.08 | 1.22 (0.65) | b | | 0.88 (0.68) | a | |

Analysis of meat quality and production traits with HMGA2 in US-Large White × Duroc.

| Trait | Mean (s.e.) | $\sigma_p$ | No. animals | | | LSmeans (s.e.) | | | geno | α | | δ | |
|---|---|---|---|---|---|---|---|---|---|---|---|---|---|
| | | | 11 | 12 | 22 | 11 | 12 | 22 | p | trait (s.e.) | p | trait (s.e.) | p |
| Hpromeat | 53.77 (0.45) | 7.57 | 55 | 147 | 83 | 54.78 (1.06)e | 51.81 (0.68)f i | 55.05 (0.88)j | 0.002 | 0.13 (0.67) | | −2.07 (0.58) | f |
| Hprorib | 15.07 (0.26) | 4.03 | 48 | 125 | 63 | 13.89 (0.71)c e | 15.18 (0.48)d | 15.76 (0.61)f | 0.09 | 0.93 (0.43) | c | 0.24 (0.36) | |
| LMprct | 45.49 (0.09) | 1.37 | 48 | 125 | 63 | 45.91 (0.22)c | 45.50 (0.15)c | 45.87 (0.19)c | 0.07 | −0.02 (0.13) | | −0.26 (0.11) | c |
| Days | 151.1 (0.65) | 8.85 | 40 | 100 | 44 | 152.0 (1.29)a | 150.6 (0.84)e | 153.8 (1.24)b f | 0.08 | 0.89 (0.85) | a | −1.56 (0.78) | c |
| LDG, g/d | 684.3 (3.35) | 57.2 | 57 | 151 | 84 | 668.0 (7.96)a | 678.9 (4.85)b | 672.8 (5.82) | 0.41 | 2.40 (4.91) | | −5.68 (4.30) | a |
| TDG, g/d | 883.3 (6.72) | 76.1 | 21 | 62 | 45 | 850.3 (13.9)c | 877.1 (8.45)da | 862.5 (10.1)b | 0.17 | 6.08 (8.55) | | 13.82 (7.41) | b |
| US_MD | 60.25 (0.59) | 6.12 | 17 | 51 | 40 | 59.61 (1.58)a | 60.12 (0.94)a | 61.88 (1.09) b | 0.35 | 1.13 (0.96) | a | −0.42 (0.77) | |

Interaction Analyses Between HMGA Genes with Fat Traits in the Reference Family

A. F2 Animals from the Berkshire and Yorkshire Crossed Family

1) Gene Frequencies

| | | Frequency | Percent | Frequency | Percent |
|---|---|---|---|---|---|
| HMGA1 | 11 | 88 | 17.85 | 88 | 17.85 |
| (Ban1) | 12 | 232 | 47.06 | 320 | 64.91 |
| | 22 | 173 | 35.09 | 493 | 100.00 |
| HMGA2 | 11 | 64 | 12.75 | 64 | 12.75 |
| | 12 | 234 | 46.61 | 298 | 59.36 |
| | 22 | 204 | 40.64 | 502 | 100.00 |

| Frequency Percent Row Pct Col Pct | | HMGA1 | | | |
|---|---|---|---|---|---|
| | | 11 | 12 | 22 | Total |
| HMGA2 | 11 | 2 | 23 | 35 | 60 |
| | | 0.41 | 4.74 | 7.22 | 12.37 |
| | | 3.33 | 38.33 | 58.33 | |
| | | 2.27 | 10.13 | 20.59 | |
| | 12 | 44 | 106 | 74 | 224 |
| | | 9.07 | 21.86 | 15.26 | 46.19 |
| | | 19.64 | 47.32 | 33.04 | |
| | | 50.00 | 46.70 | 45.53 | |
| | 22 | 42 | 98 | 61 | 201 |
| | | 8.66 | 20.21 | 12.58 | 41.44 |
| | | 20.90 | 48.76 | 30.35 | |
| | | 47.73 | 43.17 | 35.88 | |
| | Total | 88 | 227 | 170 | 485 |

| Frequency Percent Row Pct | | HMGA1 | | | |
|---|---|---|---|---|---|
| Col Pct | | 11 | 12 | 22 | Total |
| | | 18.14 | 46.80 | 35.05 | 100.00 |

B) Effect on the Last Rib Fat (lrib) Trait

Both HMG1 and HMGA2 genotypes are associated with last rib trait variation. Presence of the HMGA2 allele 2 moderately increased last rib fat content (comparing 12 and 22 genotypes). Presence of HMGA1 allele 1 shows strong association with increased fat content.

| | lrib LSMEAN | Error |
|---|---|---|
| HMGA2 | | |
| 11 | 3.18575614 | 0.11603336 |
| 12 | 3.12045322 | 0.04885318 |
| 22 | 3.22801544 | 0.04984788 |
| HMGA1 | | |
| 11 | 3.35804436 | 0.07798118 |
| 12 | 3.16165424 | 0.04771340 |
| 22 | 3.07576363 | 0.04890591 |

| Last rib HMGA2 | HMGA1 11 | 12 | 22 |
|---|---|---|---|
| 11 | 3.38 | 3.21 | 2.96 |
| 12 | 3.28 | 3.14 | 3.00 |
| 22 | 3.44 | 3.20 | 3.21 |

3) Effect on the Lumbar Fat (lum) Trait

Both HMGA1 and HMGA2 genotypes shows an association with the lumbar fat. The result of the HMGA1 and HMGA2 combination shows clearly additive effect on lumbar fat.

|  | lum LSMEAN | Error |
|---|---|---|
| HMGA2 |  |  |
| 11 | 3.47003685 | 0.13421404 |
| 12 | 3.53704166 | 0.05650774 |
| 22 | 3.55401930 | 0.05765829 |
| HMGA1 |  |  |
| 11 | 3.77507026 | 0.08990991 |
| 12 | 3.55616811 | 0.05501209 |
| 22 | 3.39947934 | 0.05638702 |

| Lum fat HMGA2 | HMGA1 11 | 12 | 22 |
|---|---|---|---|
| 11 | 3.65 | 3.72 | 3.31 |
| 12 | 3.69 | 3.60 | 3.39 |
| 22 | 3.91 | 3.63 | 3.50 |

C) Effect on the Total Lipid (tlip) Trait

The HMGA2 genotypes are associated with the total lipid variation.

|  | tlip LSMEAN | Error |
|---|---|---|
| HMGA2 |  |  |
| 11 | 2.88214497 | 0.23811466 |
| 12 | 3.06472896 | 0.10025272 |
| 22 | 3.23158737 | 0.10229396 |
| HMGA1 |  |  |
| 11 | 3.33719722 | 0.16344925 |
| 12 | 3.03313238 | 0.10000771 |
| 22 | 3.10162605 | 0.10250722 |

| HMGA2 | HMGA1 11 | 12 | 22 |
|---|---|---|---|
| 11 | 2.83 | 2.56 | 3.04 |
| 12 | 3.25 | 2.91 | 3.15 |
| 22 | 3.46 | 3.38 | 2.99 |

5) Effect on the $10^{th}$ Rib Fat (trib) Trait

The HMGA1 genotypes are significantly associated with $10^{th}$ rib fat.

|  | trib LSMEAN | Error |
|---|---|---|
| HMGA2 |  |  |
| 11 | 3.00876115 | 0.13088375 |
| 12 | 3.08337129 | 0.05507852 |
| 22 | 3.11863733 | 0.05619663 |
| HMGA1 |  |  |
| 11 | 3.28558871 | 0.08686549 |
| 12 | 3.07574337 | 0.05310117 |
| 22 | 2.98812120 | 0.05442963 |

| 10th rib HMGA2 | HMGA1 11 | 12 | 22 |
|---|---|---|---|
| 11 | 3.05 | 3.20 | 2.95 |
| 12 | 3.26 | 3.11 | 2.94 |
| 22 | 3.35 | 3.23 | 3.02 |

1. Genetic Map of the Pig Chromosome 1 in the Berkshire and Yorkshire Crossed Family Sex_Averaged Map (Recomb. Frac., Kosambi cM):

| 9 | SW1515 |  |  | 0.0 |
|---|---|---|---|---|
|  |  | 0.17 | 17.3 |  |
| 2 | S0316 |  |  | 17.3 |
|  |  | 0.03 | 3.4 |  |
| 11 | SWR2300 |  |  | 20.8 |
|  |  | 0.11 | 10.9 |  |
| 10 | S0008 |  |  | 31.6 |
|  |  | 0.16 | 16.0 |  |
| 4 | SW781 |  |  | 47.7 |
|  |  | 0.04 | 4.3 |  |
| 8 | S0312 |  |  | 51.9 |
|  |  | 0.13 | 13.4 |  |
| 7 | S0331 |  |  | 65.4 |
|  |  | 0.03 | 3.3 |  |
| 1 | MC4R |  |  | 68.6 |
|  |  | 0.04 | 4.0 |  |
| 0 | HMGA2 |  |  | 72.6 |
|  |  | 0.15 | 15.2 |  |
| 6 | SW974 |  |  | 87.8 |
|  |  | 0.17 | 17.1 |  |
| 3 | SW373 |  |  | 104.9 |
|  |  | 0.22 | 23.0 |  |
| 5 | SW1301 |  |  | 128.0 |

* denotes recomb. frac. held fixed in this analysis

Log 10_Like=−1425.68

Sex-Specific Map (Recomb. Frac., Kosambi cM—Female, Male):

| 9 | SW1515 |  |  | 0.0 |  |  | 0.0 |
|---|---|---|---|---|---|---|---|
|  |  | 0.19 | 19.7 |  | 0.15 | 14.9 |  |
| 2 | S0316 |  |  | 19.7 |  |  | 14.9 |
|  |  | 0.03 | 3.2 |  | 0.02 | 2.3 |  |
| 11 | SWR2300 |  |  | 22.9 |  |  | 17.2 |
|  |  | 0.08 | 7.6 |  | 0.16 | 16.1 |  |
| 10 | S0008 |  |  | 30.5 |  |  | 33.3 |
|  |  | 0.16 | 16.6 |  | 0.14 | 14.8 |  |

-continued

| 4 | SW781 | | 47.1 | | 48.1 |
|---|---|---|---|---|---|
| | 0.02 | 2.0 | | 0.07 | 7.0 |
| 8 | S0312 | | 49.1 | | 55.1 |
| | 0.22 | 23.4 | | 0.04 | 4.1 |
| 7 | S0331 | | 72.5 | | 59.2 |
| | 0.04 | 4.5 | | 0.02 | 2.1 |
| 1 | MC4R | | 77.0 | | 61.3 |
| | 0.06 | 5.6 | | 0.02 | 2.2 |
| 0 | HMGA2 | | 82.5 | | 63.5 |
| | 0.20 | 21.3 | | 0.09 | 9.5 |
| 6 | SW974 | | 103.8 | | 73.0 |
| | 0.20 | 21.6 | | 0.13 | 13.3 |
| 3 | SW373 | | 125.4 | | 86.3 |
| | 0.19 | 19.4 | | 0.24 | 26.4 |
| 5 | SW1301 | | 144.8 | | 112.7 |

* denotes recomb. frac. held fixed in this analysis

Log__Like=_1396.97

2. Genetic Map of the Pig Chromosome 7 in the Berkshire and Yorkshire Crossed Family See FIG. 5

Sex_Averaged Map (Recomb. Frac., Kosambi cM):

| 10 | S0025 | 0.0 |
|---|---|---|
| 0.27 | 29.7 | |
| 9 | S0064 | 29.7 |
| 0.17 | 18.1 | |
| 8 | TNFB | 47.8 |
| 0.04 | 4.4 | |
| 0 | HMGA1 | 52.3 |
| 0.12 | 12.5 | |
| 7 | SWR1928 | 64.7 |
| 0.10 | 9.7 | |
| 2 | SW2040 | 74.4 |
| 0.09 | 9.0 | |
| 5 | SW252 | 83.5 |
| 0.06 | 6.1 | |
| 1 | SW632 | 89.6 |
| 0.05 | 5.5 | |
| 4 | SW1083 | 95.1 |
| 0.20 | 21.6 | |
| 3 | S0101 | 116.7 |
| 0.21 | 22.6 | |
| 6 | SW764 | 139.3 |

* denotes recomb. frac. held fixed in this analysis

Log_Like=−1441.45

Sex-Specific Map (Recomb. Frac., Kosambi cM—Female, Male):

| 10 | S0025 | 0.0 | 0.0 | 0.30 | 35.4 | 0.23 | 24.9 |
|---|---|---|---|---|---|---|---|
| 9 | S0064 | 35.4 | 24.9 | 0.14 | 14.2 | 0.21 | 22.1 |
| 8 | TNFB | 9.6 | 47.0 | 0.06 | 5.6 | 0.04 | 3.5 |
| 0 | HMGA1 | 55.2 | 50.5 | 0.17 | 17.8 | 0.08 | 7.9 |
| 7 | SWR1928 | 72.9 | 58.4 | 0.08 | 7.8 | 0.12 | 11.9 |
| 2 | SW2040 | 80.7 | 70.3 | 0.12 | 12.1 | 0.06 | 5.9 |
| 5 | SW252 | 92.9 | 76.2 | 0.09 | 9.0 | 0.04 | 3.8 |
| 1 | SW632 | 101.8 | 80.0 | 0.05 | 5.0 | 0.06 | 6.3 |
| 4 | SW1083 | 106.9 | 86.3 | 0.21 | 21.8 | 0.20 | 21.3 |
| 3 | S0101 | 128.7 | 107.6 | 0.25 | 27.3 | 0.17 | 17.8 |
| 6 | SW764 | 156.0 | | 125.5 | | | | log10__like = −1428.65

Additional Primers and New Sequences for HMGA1

Primers:

SEQ ID NO:7
HMA1-F1 (forward) 5' AAG CAG CCT CCG GTG AGT C 3'

SEQ ID NO:8
HMA1-R1 (forward) 5' CAC TTC GCT GGG CTC CTT CT 3'
Located in exon 5 to intron 5
(~1800 bp, annealing temperature ($T_a$) is 65°)

SEQ ID NO:9
HM766F (forward) 5' TCT CTA GTT CCT CAT TCC 3'

SEQ ID NO:10
HM766R (forward) 5' CCC AAG ACA GAA TAA AAA G 3'
Located both within intron 5
(~800 bp, $T_a$ is 51.7°)

SEQ ID NO:11
HM867F (forward) 5' CCT CTT GTC ATT TTA CTG TC 3'

SEQ ID NO:12
HM867R (forward) 5' ACC CCA CTT TCC TCA ACT 3'
Located in intron 5 to intron 6
(~390 bp, $T_a$ is 57.4°)

SEQ ID NO:13
HM978F (forward) 5' CTC TGC CTC CAC TCT CTA 3'

SEQ ID NO:14
HM978R (forward) 5' TGC CAA AGG TGA CAA GAC 3'
Located both within intron 5
(~1000 bp, $T_a$ is 59.3°)

SEQ ID NO:15
HMAI2F (forward) 5' CCA GGA AGG AAA CCA AGG G 3'

SEQ ID NO:16
HMAI2R (forward) 5' TGA CTC AGC AAC CTC CAC G 3'
Located in exon 7 to intron 7
(~1200 bp, $T_a$ is 60°)

SEQ ID NO:17
HMAI2F (forward) 5' CCA GGA AGG AAA CCA AGG G 3'

SEQ ID NO:18
HMAI3R (forward) 5' TGA CTC AGC AAC CTC CAC G 3'
Located in exon 7 to intron 7
(~800 bp, $T_a$ is 56°)

PCR Conditions:

| Mix 1 | |
|---|---|
| 10 × PCR Buffer | 1.0 μl |
| MgCl$_2$ (25 mM) | 0.6 μl |
| dNTPs (2.5 mM) | 0.5 μl |
| HMGY1 (25 pmol/μl) | 0.1 μl |
| HMYS 2 (25 pmol/μl) | 0.1 μl |
| Taq Polymerase (5 U/μl) | 0.07 μl |
| ddH$_2$O | 7.63 μl |
| genomic DNA | 1.0 μl |

Combine the Mix 1 and DNA in a PCR reaction tube. Overlay mix with mineral oil. Run the following PCR program: 94° C. for 3 min; 36 cycles of 94° C. for 30 sec, $T_a$ for 1 min, and 72° C. for 1 min 40 sec; followed by a final extension at 72° C. for 10 min. Check 2 µl of the PCR on a 1.6% agarose gel to confirm amplification success and the desirable clean result in the negative control. (Each primer set was run on the program with appropriate annealing temperatures as stated in parenthesis above).

Note: Additional SNPS were identified by sequence analysis. SNP positions are indicated by bold font.

Comparison of Contig Sequence Across Breed and Consensus Sequence for HMGA1

Note: Additional SNPS were identified by sequence analysis. Sequencing of four different breeds of pigs revealed several polymorphisms in the DNA sequence of the HMGA1 gene. SNP positions are indicated by the symbol (*, +) and arrow. Description of SNPs follows.

Friedmann, M., Holth, L. T., zoghbi, H. Y., Reeves, R. 1993. Organization, inducible-expression and chromosome localization of the human HMGI(Y) nonhistone protein gene. Nucleic Acids Res. 21, 4259–4267.

Hess, J. L. 1998. Chromosomal translocaitons in benign tumors. Am. J. Clin. Path. 109, 251–261.

Melillo, R. M,, Pierantoni, G. M,, Scala. S., Battista, S., Fedele, M., Stella, A., De Biasio, M. C., Chiappetta, G., Fidanza, V., Condorelli, G., Santoro, M., Croce, C. M., Viglietto, G., Fusco, A. 2001. Critical role of the HMGI (Y) proteins in adipocytic cell growth and differentiation. Mol. Cell. Biol. 21, 2485–2495.

TABLE 1

Description of location and base change of new SNPs identified by sequence analysis for Contig 1 and 2

|  | Position | SNP | Location |  | Position | SNP | Location |
|---|---|---|---|---|---|---|---|
| Contig 1 | 197 | G/T | Intron 5 | Contig 1 | 1391 | A/G | Intron 5 |
|  | 259 | C/T | Intron 5 |  | 1564 | A/C | Intron 5 |
|  | 309 | G/A | Intron 5 |  | 1643 | G/A | Intron 5 |
|  | 913 | T/C | Intron 5 |  | 1784 (BanI) | C/T | Exon 6 |
|  | 1004 | T/G | Intron 5 |  | 1848 | A/C | Intron6 |
|  | 1028 | T/C | Intron 5 |  | 2306 (NaeI) | C/T | Intron 6 |
|  | 1065 | G/A | Intron 5 |  | 2375 | T/C | Intron 6 |
|  | 1170 | G/A | Intron 5 | Contig 2 | 123 | C/A | Intron 7 |
|  | 1333 | G/A | Intron 5 |  | 762 | C/T | Intron 7 |

Note:

There are other potential SNPs for contig 2 that could not be confirm by sequence.

References

Arlotta, P., Tai, A. K., Manfioletti, G., Clifford, C., Jay, G., Ono, S. J. 2000. Transgenic mice expressing a truncated form of the high mobility group I-C protein develop adiposity and an abnormally high prevalence of lipomas. J. Biol. Chem. 275, 14394–14400.

Ashar, H. R., Fejzo, M. S., Tkachenko, A., Zhou, X., Fletcher, J. A., Weremowicz, S., Morton, C. C., Chada, K. 1995. Disruption of the architectural factor HMGI-C: DNA-binding AT hook motifs fused in lipomas to distinct transcriptional regulatory domains. Cell 82:57–65.

Bustin, M., 2001. Revised nomenclature for high mobility group (HMG) chromosomal proteins. Trends Biochem. Sci. 26, 152–153.

Tallini, G., Dal Cin, P. 1999. HMGI(Y) and HMGI-C dysregulation: a common occurrence in human tumors. Adv. Anat. Pathod. 6, 237–246.

Reeves, R. 2000. Structure and function of the HMGI(Y) family of architectural transcription and chromatin structure. Environ. Health Perspect. 108, 803–809.

Reeves, R., Beckerbauer, L. 2001. HMGI/Y proteins: flexible regulators of transcription and chromatin structure. Biochim. Biophy. Acta 1519, 13–29.

Zhou, X., Benson, K. F., Ashar, H. R., Chada, K. 1995. Mutation responsible for the mouse pygmy phenotype in the developmentally regulated factor HMGI-C. Nature 376, 771–774.

What is claimed is:

1. A method of identifying a genetic marker correlated with favorable growth, fatness, meat quality, or feed efficiency traits in pigs of a particular breed, strain, population, or group comprising the steps of:
obtaining a sample of genetic material from a representative sample of pigs from said breed, strain, population or group, said sample comprising a HMGA1 gene; comprising a sequence set forth in one of SEQ ID NOS:19, 21–29;
assaying said sample for the presence of a polymorphic allele in said HMGA1 gene; and
correlating whether a statistically significant association exists between said polymorphic allele and favorable growth, fatness, meat quality, or feed efficiency traits in said breed, strain, population or group, pigs can be characterized for said genetic markers if said correlation exists.

2. The method of claim 1 wherein said assaying is selected from the group consisting of: single-strand conformation polymorphism (SSCP) analysis, base excision sequence scanning (BESS), restriction fragment length polymorphism (RFLP) analysis, heteroduplex analysis, denaturing gradient gel electrophoresis (DGGE), temperature gradient electrophoresis, allelic polymerase chain reaction (PCR), ligase chain reaction direct sequencing, mini sequencing, nucleic acid hybridization, or micro-array-type detection of said HMGA1 gene.

3. The method of claim 1 wherein said genetic marker comprises a single nucleotide polymorphism.

4. The method of claim 1 wherein said HMGA1 gene contains a Nae I polymorphism.

5. The method of claim 1 wherein said HMGA1 gene contains a Ban I polymorphism.

6. The method of claim 1 further comprising PCR amplifying an amount of said HMGA1 gene or a portion thereof which contains said polymorphic allele.

7. The method of claim 6 wherein said PCR amplification includes selecting a forward and reverse primer capable of amplifying an amount of said HMGA1 gene or a portion thereof which contains said polymorphic allele.

8. The method of claim 7 wherein said primer is selected from or based upon SEQ ID NO:1 and SEQ ID NO:2.

9. The method of claim 7 wherein said primer is selected from or based upon SEQ ID NO:7 and SEQ ID NO:8.

10. The method of claim 7 wherein said primer is selectged from or based upon SEQ ID NO:9 and SEQ ID NO:10.

11. The method of claim 7 wherein said primer is selected from or based upon SEQ ID NO:11 and SEQ ID NO:12.

12. The method of claim 7 wherein said primer is selected from or based upon SEQ ID NO:13 and SEQ ID NO:14.

13. The method of claim 7 wherein said primer is selected from or based upon SEQ ID NO:15 and SEQ ID NO:16.

14. The method of claim 7 wherein said primer is selected from or based upon SEQ ID NO:17 and SEQ ID NO:18.

* * * * *